United States Patent
McAlary et al.

(10) Patent No.: US 10,060,259 B2
(45) Date of Patent: *Aug. 28, 2018

(54) PASSIVE SAMPLING DEVICE AND METHOD OF SAMPLING AND ANALYSIS

(71) Applicants: Geosyntec Consultants, Inc., Boca Raton, FL (US); Suresh Seethapathy, Annapolis, MD (US); Tadeusz Gorecki, Waterloo (CA)

(72) Inventors: Todd Arthur McAlary, Mississauga (CA); Suresh Seethapathy, Annapolis, MD (US); Tadeusz Gorecki, Waterloo (CA)

(73) Assignee: Geosyntec Consultants, Inc. (CA)

( * ) Notice: Subject to any disclaimer, the term of this patent is extended or adjusted under 35 U.S.C. 154(b) by 95 days.

This patent is subject to a terminal disclaimer.

(21) Appl. No.: 15/190,729

(22) Filed: Jun. 23, 2016

(65) Prior Publication Data

US 2016/0298450 A1 Oct. 13, 2016

Related U.S. Application Data

(63) Continuation of application No. 14/022,960, filed on Sep. 10, 2013, now Pat. No. 9,399,912.

(60) Provisional application No. 61/700,667, filed on Sep. 13, 2012.

(51) Int. Cl.
| | |
|---|---|
| *G01N 30/86* | (2006.01) |
| *E21B 49/08* | (2006.01) |
| *G01N 30/06* | (2006.01) |

(52) U.S. Cl.
CPC ............ *E21B 49/081* (2013.01); *E21B 49/08* (2013.01); *G01N 30/06* (2013.01); *G01N 30/8693* (2013.01)

(58) Field of Classification Search
CPC ....................................................... E22B 48/081
See application file for complete search history.

(56) References Cited

U.S. PATENT DOCUMENTS

| | | | | |
|---|---|---|---|---|
| 5,346,005 | A * | 9/1994 | Robbins ................ | E21B 33/127 166/187 |
| 5,462,677 | A * | 10/1995 | Benesi ............... | B01D 25/1275 100/198 |
| 5,482,677 | A * | 1/1996 | Yao ...................... | G01N 1/2273 210/198.3 |
| 5,497,829 | A * | 3/1996 | Rajkovich ............... | E21B 33/02 102/333 |
| 5,992,213 | A * | 11/1999 | Tartre ........................ | B09C 1/00 73/19.01 |
| 6,226,852 | B1 * | 5/2001 | Gundel .................... | B01J 20/26 29/458 |
| 6,289,714 | B1 * | 9/2001 | Tartre ..................... | E21B 49/08 175/59 |

(Continued)

*Primary Examiner* — Harshad R Patel
*Assistant Examiner* — Tran M Tran
(74) *Attorney, Agent, or Firm* — Joan T. Kluger; Barnes & Thornburg LLP

(57) ABSTRACT

A device and method to quantitatively measure concentrations of volatile organic compound vapors below the ground surface using a preferably "fully" passive device that is placed in a drilled or bored hole for a specified period of time, wherein the sampler constrains the uptake rate to match values that minimize or eliminate the starvation effect and provide acceptable sensitivity for most soil types as calculated via mathematical models.

20 Claims, 18 Drawing Sheets

(56) References Cited

U.S. PATENT DOCUMENTS

| | | | | |
|---|---|---|---|---|
| 6,564,656 B1* | 5/2003 | Woolfenden | ........ | B01L 3/50825 |
| | | | | 73/863.21 |
| 6,607,700 B1* | 8/2003 | Apte | .................... | G01N 33/004 |
| | | | | 422/408 |
| 6,645,773 B2* | 11/2003 | Tipler | .................... | G01K 11/00 |
| | | | | 374/142 |
| 6,758,274 B2* | 7/2004 | Parent | .................... | E21B 33/128 |
| | | | | 166/242.3 |
| 7,059,206 B1* | 6/2006 | Kingston | ................. | G01N 1/12 |
| | | | | 73/64.56 |
| 7,092,077 B2* | 8/2006 | Kishkovich | ............ | B01D 53/22 |
| | | | | 356/36 |
| 7,114,370 B2* | 10/2006 | Radolovich | .......... | G01N 1/2273 |
| | | | | 73/31.03 |
| 7,222,546 B2* | 5/2007 | St. Germain | ........ | G01N 1/2294 |
| | | | | 73/863.21 |
| 7,325,443 B2* | 2/2008 | De Jonge | ................ | G01F 1/704 |
| | | | | 73/61.72 |
| 7,487,662 B2* | 2/2009 | Schabron | ............ | G01N 27/626 |
| | | | | 422/83 |
| 7,980,147 B2* | 7/2011 | Tang | .................... | G01N 1/2214 |
| | | | | 73/863.21 |
| 8,561,484 B2* | 10/2013 | Tipler | .................. | G01N 1/2214 |
| | | | | 422/430 |
| 9,399,912 B2* | 7/2016 | McAlary | ............... | E21B 49/081 |
| 2015/0300928 A1* | 10/2015 | Perez Ballesta | ..... | G01N 1/2273 |
| | | | | 73/863.23 |

* cited by examiner

PASSIVE SAMPLING DEVICE AND METHOD OF SAMPLING AND ANALYSIS

CROSS-REFERENCE TO RELATED APPLICATIONS

This application is a continuation of and claims priority to U.S. patent application Ser. No. 14/022,960, filed Sep. 10, 2013, entitled Passive Sampling Device and Method of Sampling and Analysis, and claims the benefit of U.S. Provisional Patent Application No. 61/700,667, filed Sep. 13, 2012, entitled Low-Uptake Waterloo Membrane Sampler for Quantitative Passive Soil Vapor Concentration Measurement.

This invention was made with government support under contract number W912-HQ-08-C-046 (project no. ER-0830) awarded by ESTCP and under contract number N66001-07-R-0108 awarded by Navy SPAWAR Systems Center, San Diego. The government has certain rights in the invention.

BACKGROUND OF THE INVENTION

Several different types of passive samplers are known in the art for measuring relative abundance of volatile organic compound (VOC) vapors below the ground surface, but the uptake rate of the sampler and the delivery rate of vapors to the void space in which the sampler is deployed has not been known or controlled, so the ability to quantify vapor concentrations from the mass of compounds sorbed was not very accurate or precise. As a result, they have been labeled as useful only for screening purposes and not for purposes requiring higher levels of data validation such as human health risk assessment.

Prior passive soil vapor sampling devices include the Gore® Sorber or Gore® Module, Petrex Tubes, Beacon's B-Sure Test Kit, and EMFLUX cartridges. Each of these consists of sorbent media exposed to a void space in the subsurface with no rigorous attempt to maintain an uptake rate by the sampler that is lower than the delivery rate of vapors from the soil. In this case, the uptake rate varies according to the porosity and moisture content of the soil, which is seldom consistent.

For some existing passive soil vapor samplers, concentrations can at best be estimated by deriving an empirical relationship between the mass sorbed and concentrations measured with conventional active soil gas sampling methods; however, this has limitations because the empirical relationship depends on site-specific conditions, which may vary unpredictably between sites and sampling locations. Others (e.g., the Gore™ Module) have attempted to use an equation to calculate the uptake rate from the soil moisture and porosity, but they did not derive their equations from first principles, and have not shown their approach provides accurate and precise concentration data.

What is needed is a sampler that constrains the uptake rate of the sampler to be lower than the delivery rate for most commonly encountered conditions of soil porosity and moisture content, to provide consistent quantification of soil vapor concentrations. The uptake rate must also be high enough to allow the sampler to detect low soil vapor concentrations with a practical sampling duration.

SUMMARY OF THE INVENTION

The invention provides a method to quantitatively measure concentrations of VOC vapors below the ground surface using a preferably "fully" passive (i.e., relies on diffusion and permeation only with no power, pumping or forced advection) device that is placed in a drilled or bored hole for a specified period of time, which is supported by mathematical models and controlled field experiments. For short sample periods, there is an option to purge stagnant soil gas from the void-space in which the sampler is deployed; therefore, the invention includes both fully passive methods as well as methods where forced advection is incorporated briefly at the outset of the sampling period.

In an illustrative embodiment of the invention, the sampler comprises a container filled with a sorbent medium and having an opening which may be covered with a membrane. The membrane preferably has a uniform thickness. The sorbent medium is suitable to retain and recover the target analytes using solvent extraction or thermal desorption. The sampler constrains the uptake rate to values that minimize or eliminate the starvation effect for most soil types as calculated via mathematical models. In exemplary embodiments of the invention, adequate sensitivity is provided (ability to detect low concentrations) with practical sample durations.

Two mathematical models (transient and steady-state) were used to calculate the relationship between the delivery rate of vapors to the void space in which a passive sampler is deployed and the soil moisture and porosity. The uptake rate of the sampler is similar to or smaller than the delivery rate of vapors from the surrounding soil for most commonly-encountered soil moisture contents, so the concentration of vapors in the void space within which the sampler is exposed is similar to the concentration in the surrounding soil gas throughout the majority of the sampling interval.

VOC vapor concentrations below the ground surface are measured using the inventive passive sampler to sorb (or trap) VOC vapors at known uptake rates, which allows the concentration to be calculated from the mass of each compound sorbed and the exposure time of the sample (both of which can be measured with acceptable accuracy using existing methods).

During the exposure time (also known as the sampling period, the sample duration or combinations of these terms), vapors dissolve into the membrane in the sampler and permeate across it at rates that are distinct for each chemical. The uptake rates are also proportional to the linear temperature programmed retention indices (LTPRI) of the compounds or chemicals of interest for analysis by gas chromatography where the stationary phase is the same material as used for the membrane (e.g., polydimethyl siloxane, or PDMS). The membrane area, i.e. the opening area, and the membrane thickness may be selected to optimize the uptake rate for the specific compounds or chemicals of interest.

The invention further includes a method of sampling that comprises employing a plug to seal the drillhole or borehole slightly above a passive sampler. In an illustrative embodiment of the method, a plastic sleeve is cut to a length of about 30 cm longer than the depth from the ground surface to the location where the seal is desired. A foam plug (slightly larger in diameter than the borehole) is compressed and placed inside one end of a thin walled rigid pipe. A dowel is placed inside the pipe and the pipe is positioned inside the plastic sleeve. A borehole is drilled and the soil removed. The passive sampler is then lowered to the target depth using an inert tether. The plastic sleeve, pipe and dowel are then lowered to a depth slightly above the sampler. The foam is then forced out of the pipe using the dowel. The foam expands and presses against the borehole wall and form a seal just above the passive sampler during the sampling period.

The invention includes determination of the optimal uptake rates, the samplers for quantitative passive soil vapor concentration measurement and the methods of sampler deployment, sealing, retrieval and analysis to quantitatively measure concentrations of VOC vapors below the ground surface according to any of the embodiments described herein.

DESCRIPTION OF THE DRAWINGS

Illustrative embodiments of the invention are best understood from the following detailed description when read with the accompanying drawings.

DETAILED DESCRIPTION OF THE INVENTION

Figure 1:
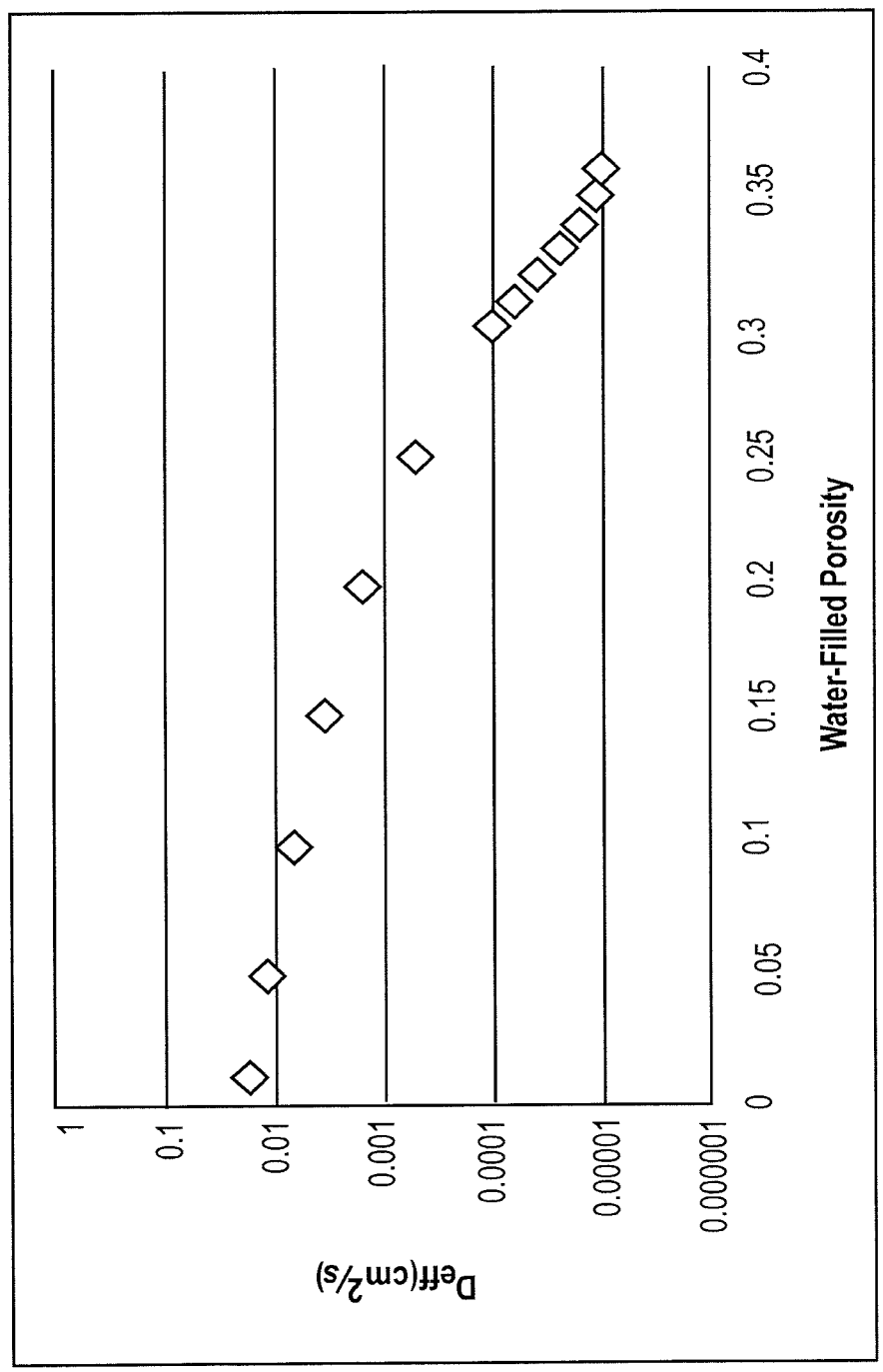
FIG. 1 shows the effective diffusion coefficient versus water-filled porosity for TCE in a soil with 37.5% total porosity, typical of a sandy soil.

The invention provides a method to quantitatively measure concentrations of VOC vapors below the ground surface using a preferably "fully" passive (i.e., relies on diffusion and permeation only) device that is placed in a drilled or bored hole for a specified period of time, supported by mathematical models and controlled field experiments. The device sorbs or traps VOC vapors at known uptake rates, which allow the concentration to be calculated from the mass of each compound sorbed (quantified by a chemical analysis laboratory) and the exposure time.

The process improvement consists of: calculations using two mathematical models (transient and steady-state) to derive the relationship between the delivery rate of vapors to the void space in which a passive sampler is deployed and the soil moisture and porosity; a new sampling device that constrains the uptake rate to a desired value, which is preferably lower than typical rates of vapor delivery to the void space via diffusion through the surrounding soil but high enough to provide acceptable sensitivity within a reasonable period of sampling, and; methods of sampler deployment, sealing, retrieval and analysis. If the uptake rate of the sampler is similar to or smaller than the delivery rate of vapors from the surrounding soil, the concentration of vapors in the void space within which the sampler is exposed will be similar to the concentration in the surrounding soil gas throughout the majority of the sampling interval. Past attempts at quantitative passive soil vapor sampling did not control the uptake rate at levels below the rate of vapor diffusion toward the sampler from the surrounding soil and therefore, likely suffered from the "starvation effect", where the concentrations of VOC vapors in the void space are lower than concentrations in the surrounding soil, resulting in a negative bias in the concentration measurements, or an inconsistent correlation between the mass sorbed per unit time and the concentration (i.e., unknown or unpredictable uptake rate). The mathematical models will now be described according to an illustrative embodiment of the invention.

Transient and steady-state mathematical models of radial vapor diffusion to a drilled hole were developed to help understand vapor transport rates during passive diffusive soil vapor sampling. These simulations provide a technical basis for the design of passive samplers in order to achieve reliable quantitative soil vapor concentrations. The sampler is designed to, and will have a known or predictable uptake rate throughout the sample duration for most commonly-encountered soil moisture and porosity conditions.

Quantitative passive samplers are of two general varieties: 1) equilibrium samplers (where the concentration in the sampler equilibrates with the surrounding medium, including a partitioning coefficient if the sampler is composed of a different medium), and 2) kinetic samplers (where the sampler is designed to have a constant uptake rate throughout the sample duration). The illustrative model deals with kinetic passive samplers.

The basic principles of operation for quantitative passive samplers are as follows. Each device is supplied by the laboratory certified clean and sealed in air-tight packing. The sampler is exposed to the air, gas or atmosphere being investigated for a measured amount of time (t), during which VOCs diffuse or permeate into the device from the surrounding gas or atmosphere in response to the chemical potential (i.e., concentration) gradient. A certain mass (M) of VOCs is sorbed (or trapped) by the sorptive medium within the device. After sampling, the mass sorbed is quantified. The time-weighted average (TWA) concentration (C) of a particular analyte in the medium being sampled is then calculated as follows:

$$C = \frac{M}{UR \times t} \quad (1)$$

where:
C=TWA concentration in the sampled air [$\mu g/m^3$]
M=mass of analyte on the sorbent, blank-corrected if needed [pg]
UR=passive sampler uptake rate [mL/minute]
t=sampling time or exposure duration [minutes]
(note that there are two offsetting conversion factors from pg to $\mu g$ and mL to $m^3$)

The UR has units of vol/time, but it is important to recognize that it does not represent a flow rate (sampling occurs by diffusion and permeation only, with no net flow of gas); rather, it is simply a number equivalent to the flow rate that would produce the same mass loading on an active sampler that had air pulled through it for the same C and t. The mass sorbed and exposure duration are both measured by conventional methods with acceptable accuracy, so the uptake rate is a key factor controlling the accuracy of the calculated concentration. Quantitative passive samplers are designed to control the uptake rate of chemicals using a fixed cross-sectional opening area and diffusion or permeation characteristics for the chemicals of interest. The opening area may include a single hole or a plurality of holes. Uptake rates are typically measured in controlled chambers, where the concentration is known, to calibrate the samplers for particular chemicals and sampling conditions.

High uptake rates generally provide greater sensitivity (i.e., allow lower concentrations to be quantified with shorter exposure duration), which can be an advantage in some instances. Lower uptake rates reduce the risk of the "starvation effect", which occurs when the rate-limiting step is transport of chemicals to the sampler instead of the uptake rate of the sampler itself. This situation results in a reduction in vapor concentrations near the sampler, and a negative bias in the calculated passive sampler concentrations compared to the conditions under which the passive sampler was calibrated. Advection from wind and ventilation during indoor and outdoor air sampling is often sufficient to minimize the starvation effect. For soil gas sampling, advection is likely to be minimal and the rate of contaminant vapor replenishment in the gas-filled void space surrounding the sampler is likely to be limited to diffusive transport only, which is the focus of the mathematical models presented here. The uptake rate of the sampler can be increased or decreased by design (such as by area and thickness of the membrane, for example) to minimize the starvation effect and provide acceptable sensitivity.

Model for Quantitative Passive Soil Vapor Sampling

Passive soil vapor sampling is usually performed by drilling a hole in the ground, removing soil, placing a passive sampler in the void space created by drilling, sealing the hole from the atmosphere for the duration of the exposure, then retrieving the sampler and backfilling or grouting the hole. A simple conceptual model of this scenario is as follows:

Immediately after the hole is drilled and the soil is removed, the void space fills with air. Assuming atmospheric air can enter the void space with less resistance than gas flowing through the surrounding soil, the initial concentration of vapors inside the void space would be expected to be much lower than that in the surrounding soil, and at worst could be assumed to be essentially zero (i.e., atmospheric air is nearly contaminant-free).

In most cases, passive samplers are emplaced and the space above them is sealed without purging to attempt to remove atmospheric air from the void space around the sampler. In conventional passive soil vapor sampling methods, the seal has typically been placed at the ground surface, so the void-space is exposed to soil over the entire depth of the drillhole or borehole. This invention includes a method for setting a seal at a depth just above the sampler to provide better vertical resolution of vapor concentrations. Purging may not be required if the sampling duration is long compared to the time required for vapor concentrations in the void-space to equilibrate with the surrounding soil (which is the focus of the transient model). Purging can be added as a step after passive sampler deployment if, for example, the sampling period is short compared to the equilibration time.

During the period of passive sampling, vapors diffuse into the void space from the surrounding soil. If the void space is long relative to its diameter and short enough that the geologic properties and vapor concentrations are relatively uniform over the vertical interval of the void space, then the diffusion will be essentially radially symmetric (this has been assumed for both the transient and steady-state models).

The rate of diffusive mass transport into the void space over time will depend on the concentration gradient and effective diffusion coefficient, and will gradually diminish as the concentration in the void space increases (i.e., the concentration gradient decreases, which is the driving force for diffusion). The concentration in the void space will eventually stabilize at a concentration slightly below the concentration in the surrounding soil as long as some mass is being removed by a passive sampler.

If the uptake rate of the sampler is small relative to the rate of diffusion into the void space (a goal if the starvation effect is to be small), then the steady-state concentration in the void space will be similar to the concentration in the surrounding soil, which is important for accuracy of the concentrations measured via passive sampling.

Mathematical Modeling of Quantitative Passive Sampling

Passive soil vapor sampling involves: a) transport of vapors through the soil surrounding the drill-hole into the void space in which the sampler is deployed; b) diffusion through the air inside the void space, and; c) uptake by the sampler. The free-air diffusion coefficient through the air inside the void space will generally be much higher than the effective diffusion coefficient in the surrounding soil, so vapor transport through the air inside the void space is not expected to be the rate-limiting step. This allows the mathematical analysis to focus on two components: The rate of vapor diffusion into the void space (the "diffusive delivery rate", or DDR) and the rate of vapor uptake by the passive sampler ("passive sampler uptake rate" or UR). Understanding the rate of diffusion of vapors into the void space is necessary to design an appropriate uptake rate for the passive sampler, which both minimizes the starvation effect and provides adequate sensitivity (ability to meet target reporting limits with acceptable sample durations).

Influence of Soil Moisture on the Effective Diffusion Coefficient in Soil

The effective diffusion coefficient depends on the total porosity and water-filled porosity. Understanding this relationship is helpful for context in the theory of passive soil gas sampling if diffusion is the main process delivering vapors to the void space in which the sampler is deployed. P. C. Johnson and R. A. Ettinger have used equation (2) to calculate the effective diffusion coefficient for subsurface gaseous and aqueous phase diffusion.

$$D_{eff} = \frac{D_{air}\theta_a^{10/2}}{\theta_T^2} + \frac{D_w\theta_w^{10/3}}{\theta_T^2} \quad (2)$$

Where
- $D_{eff}$ is the effective diffusion coefficient [cm²/s]
- $D_a$ is the free-air diffusion coefficient [cm²/s]
- $\theta_a$ is the air-filled porosity (volume of air/total volume of soil: dimensionless),
- $D_w$ is the aqueous diffusion coefficient [cm²/s],
- $\theta_w$ is the water-filled porosity (volume of water/total volume of soil: dimensionless),
- $\theta_T$ is the total porosity ($\theta_a + \theta_w$), and
- H is the Henry's Law Constant (concentration in gas/concentration in water).

Equation 2 was used to calculate $D_{eff}$ for both transient and steady-state models. Parameter values used for all calculations were selected to be representative of trichloroethene (TCE, a common VOC) and are presented in Table 1.

TABLE 1

Parameter Values used in Model Simulations (representative for TCE)

| Parameter name | Symbol | Units | Value |
|---|---|---|---|
| Free air diffusion coefficient | $D_{air}$ | cm²/s | 0.069 |
| Aqueous diffusion coefficient | $D_w$ | cm²/s | 0.00001 |
| Henry's Law Constant (15° C.) | H | dimensionless | 0.40 |
| Total porosity | $\theta_T$ | Volume of voids/total | 0.375 |
| Water-filled porosity | $\theta_w$ | Volume of water/total volume of soil | Various values from 0.01 to 0.36 |

A series of calculations were performed using Equation (2) and the parameter values in Table 1 to show the relationship between the effective diffusion coefficient and the water-filled porosity. The calculated $D_{eff}$ values span a range from about 0.01 to about 0.00001 cm²/s over a range of water-filled porosities from 1% to 36% in a soil with 37.5% porosity as shown in FIG. 1. These values are indeed much lower than the free-air diffusion coefficient (0.069 cm²/s), which supports the assumption that diffusion through the void space in which the sampler is deployed is not rate-limiting (which is consistent with the assumption stated above). Other VOCs have similar diffusion coefficients, so the general trends apply for most VOCs of interest for human health risk assessments.

FIG. 1 shows the difference between the effective diffusion coefficient of dry soils as compared to wet soils is a factor of more than 1,000. Passive samplers generally should be designed to accommodate the widest practical range of soil moisture conditions to have broad applicability.

Two models (transient and steady-state) are presented to simulate the passive sampling process.

Transient Model

Figure 2:
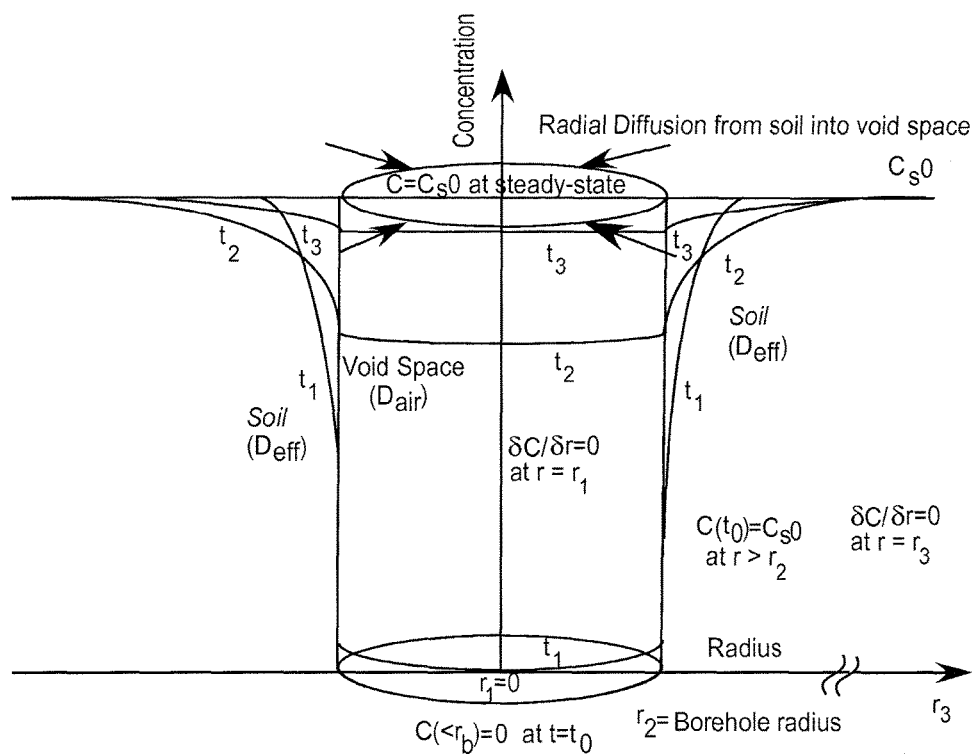
FIG. 2 is a schematic of the transient mathematical model domain including boundary and initial conditions according to an illustrative embodiment of the invention.

The conceptualization for the transient mathematical model of radial diffusion of vapors from soil into the void space is shown in FIG. 2. The mathematical model corresponding to FIG. 2 allows the diffusive delivery rate of vapors from the soil to the void-space in which the sampler is deployed to be calculated for different soil water-filled porosity values, borehole diameters and chemical properties. FIGS. 2-6 refer to the transient model.

Transient Model Simulations

A series of simulations were performed using the transient model to show the relationship between the mass entering the void space from the surrounding soil and time. These simulations initially do not account for mass removed by a passive sampler in the borehole, which would draw a small but finite amount of mass from the surrounding soil over time. The effect of adding a sampler is considered later.

Equation (1) can be re-arranged to express the diffusive delivery rate (DDR) to the void space as a function of the initial concentration of vapor in the soil ($C_s^0$) and the mass of vapors entering the void space from the surrounding soil ($M_v$) during the deployment time (t), i.e.:

$$DDR = \frac{M}{C_s^0 t} \quad (3)$$

Figure 3:
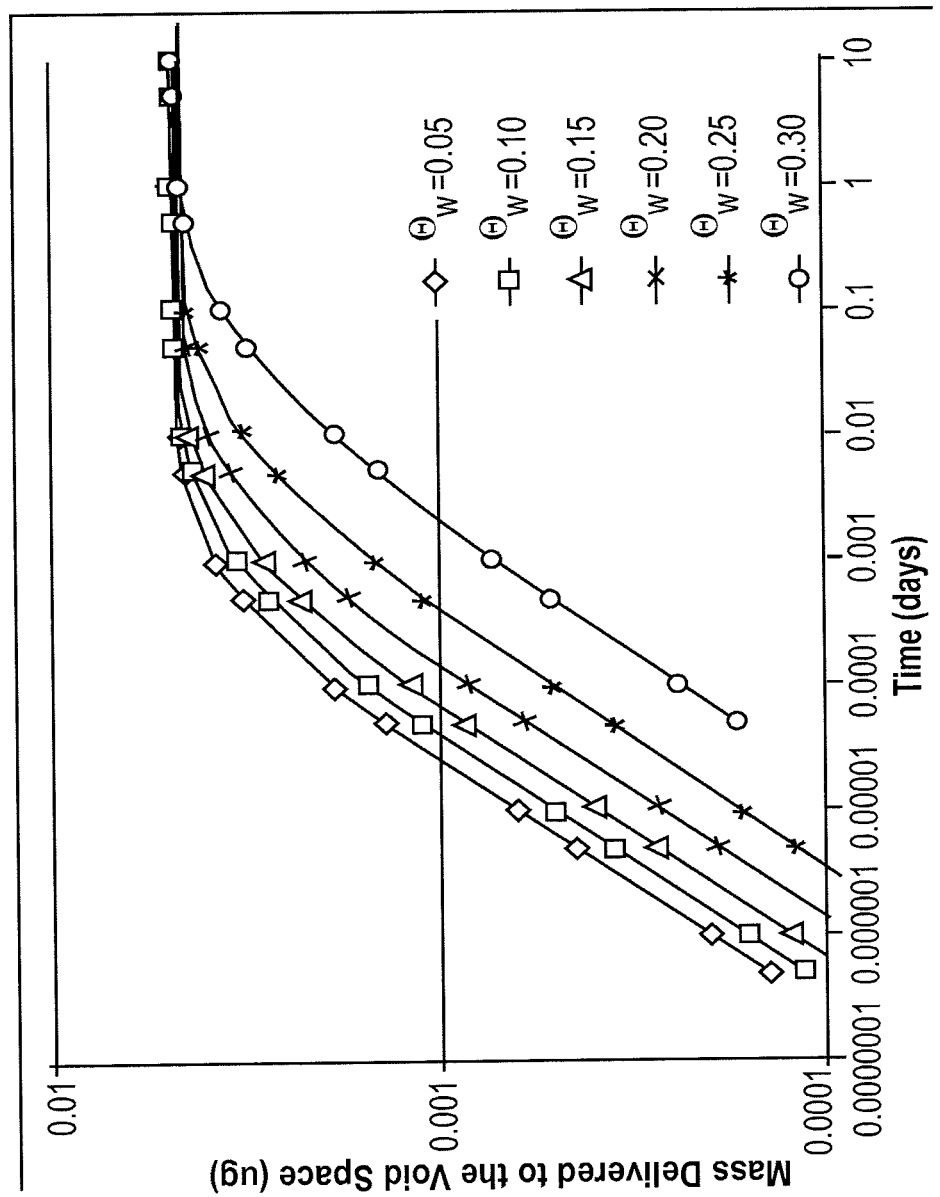
FIG. 3 shows the simulated mass of TCE delivered by diffusion from surrounding soil to the void space versus time for range of water-filled porosities in a 10 cm tall and 2.5 cm diameter void-space in a sandy soil with 37.5% total porosity and an initial soil vapor concentration of 100 $\mu g/m^3$, assuming no removal of mass by a passive sampler.

Equation 3 provides a basis for calculating a DDR value that can be compared to the sampler uptake rate directly, which is useful for identifying the threshold uptake rate needed to minimize the starvation effect. The mass entering the void space as a function of time is shown in FIG. 3 for a 2.54 cm (1-inch) diameter drill-hole, a $C_s^0$ of 100 μg/m³ and a vertical interval of 10 cm, including simulations for a variety of different water-filled porosities ($\theta_w$) and the corresponding effective diffusion coefficients ($D_{eff}$) from FIG. 1. For all water contents simulated, the mass eventually reaches a steady value as the concentration inside the void space equilibrates with the surrounding soil. This is only representative of a borehole with no passive sampler; however, the simulation is nevertheless instructive because it provides information on the time required for the void space to equilibrate with the surrounding soil as a function of the moisture content. For relatively dry soils (e.g., $\theta_w < 0.1$), the void space concentration would be within 10% of the soil vapor concentration in as little as about 10 minutes. For very wet soils (e.g., $\theta_w$=0.30), a similar level of equilibration may require up to about one day. FIG. 3 shows that the void-space equilibrates quickly with the surrounding soil vapor concentrations (within about an hour or less for all but very wet soils).

Figure 4:
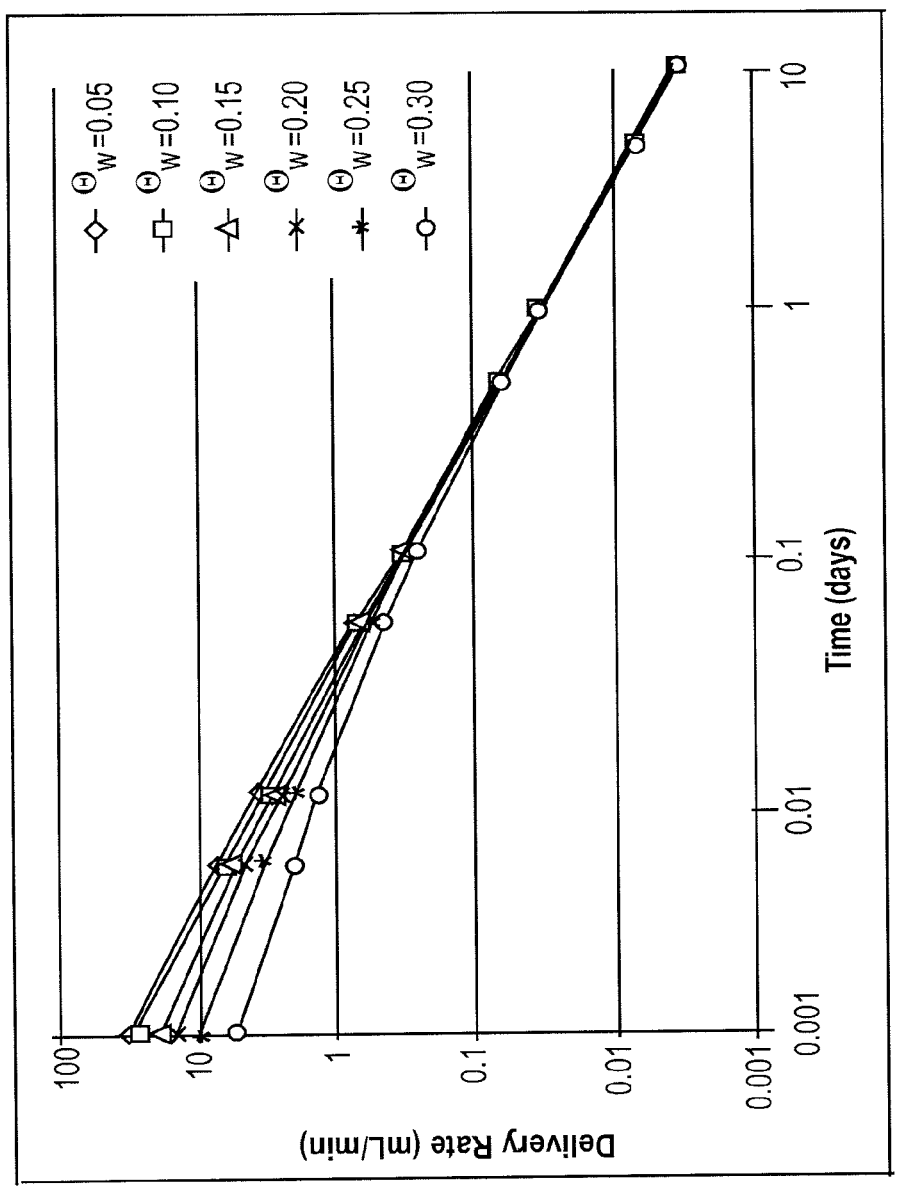
FIG. 4 shows the diffusive delivery rate of TCE versus time for a range of water-filled porosities for mass entering void space of a 10 cm tall and 2.5 cm diameter void-space in a soil with 37.5% total porosity and an initial soil vapor concentration of 100 $\mu g/m^3$, assuming no removal of mass by a passive sampler.

The simulation results shown in FIG. 3 can also be used to calculate the corresponding diffusive delivery rates of vapors from soil into the void space via Equation (3), as shown in FIG. 4. FIG. 4 shows the diffusive delivery rate is in the range of about 0.1 to 10 mL/min during the period over which the void-space equilibrates with the surrounding soil vapor concentrations (about 0.1 day or less for all but very wet soil as per FIG. 3). The diffusive delivery rate decreases as the vapor concentration in the void space approaches equilibrium with the surrounding soil because the concentration gradient (which is the driving force for diffusion) diminishes. For an equilibration time of 10 minutes or less (corresponding to the equilibration time for dry soil), the diffusive delivery rate from the soil to the void space calculated using Equation (3) is about 5 mL/min. For an equilibration time of about one day (corresponding to the equilibration time for a very wet soil), the diffusive delivery rate is about 0.03 mL/min. Note that these simulations assume there is no passive sampler in the void space. Adding a sampler would remove a certain amount of VOC mass, which would sustain a higher concentration gradient and the average diffusive delivery rate would be higher than simulated by this model, especially for longer-term deployment intervals. Nevertheless, this provides an initial framework for designing a preferred uptake rate for a passive sampler for quantitative soil vapor concentration measurement.

Figure 5:
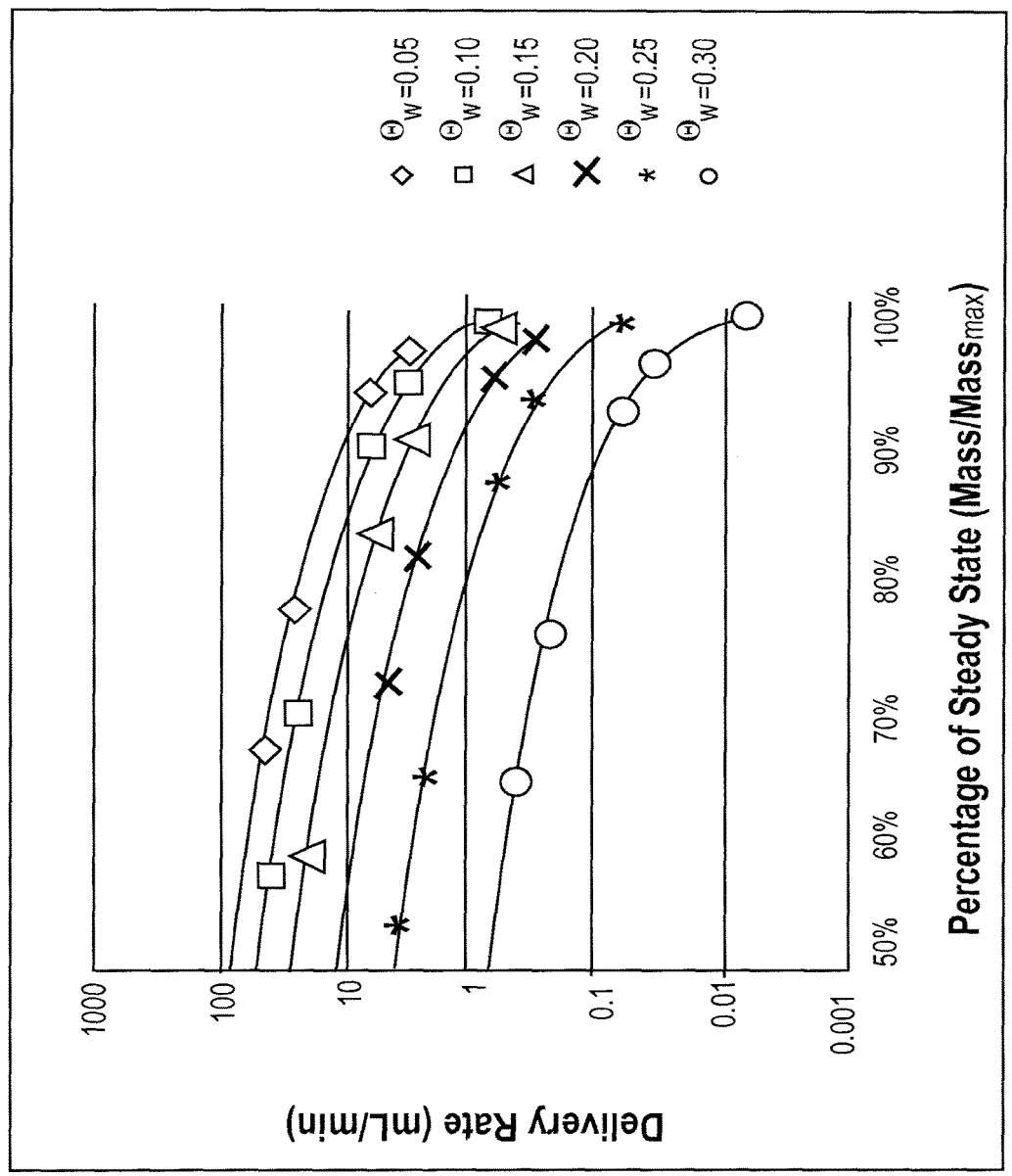
FIG. 5 shows the relationship between the instantaneous diffusive delivery rate of TCE vapors into the void space versus the percent of mass entering the void space for different water-filled porosities, where $Mass_{max}$, is the maximum vapor mass in the void space at equilibrium, assuming a 2.5 cm diameter borehole in a soil with 37.5% total porosity, initial soil vapor concentration of 100 $\mu g/m^3$ and no removal of mass by a passive sampler.

In absence of a passive sampler inside the void space, the diffusive delivery rate (DDR) gradually slows down as the concentration inside the void approaches the concentration in the surrounding soil and the concentration gradient diminishes. The relationship between the average DDR and the percentage of the total mass transferred from the soil to the void space is shown in FIG. 5. FIG. 5 shows that the diffusive delivery rate is above 1 mL/min, except for very wet soils and when the vapor concentration in void-space is very close to the concentration in the surrounding soil (i.e., when the concentration gradient driving the diffusion has diminished to a very low level).

For very dry soils, the average DDR is greater than 10 mL/min until about 90% of the mass has entered the void space. In this scenario, a passive sampler with an uptake rate of 10 mL/min may still provide data with an acceptably small starvation effect (i.e., the sampler uptake rate remains below the diffusive delivery rate from the soil until the mass delivered to the void space is about 90% of the steady-state value, so a negative bias of only 10% or less may be possible. For very wet soils ($\theta_w$=0.30), the average DDR is about 0.01 mL/min by the time the void space has nearly equilibrated with the surrounding soil (roughly 1 day). However, for moisture contents typical of most vadose zone soils, an uptake rate of about 1 mL/min would be expected to result in an acceptably small starvation effect (i.e., for a water-filled porosity of up to 25% in a soil with 37.5% porosity, a sampler with an uptake rate of 1 mL/min would be expected to result in less than 20% negative bias via the starvation effect).

Superposition of Diffusive Delivery Rate and Uptake Rate

Figure 6:
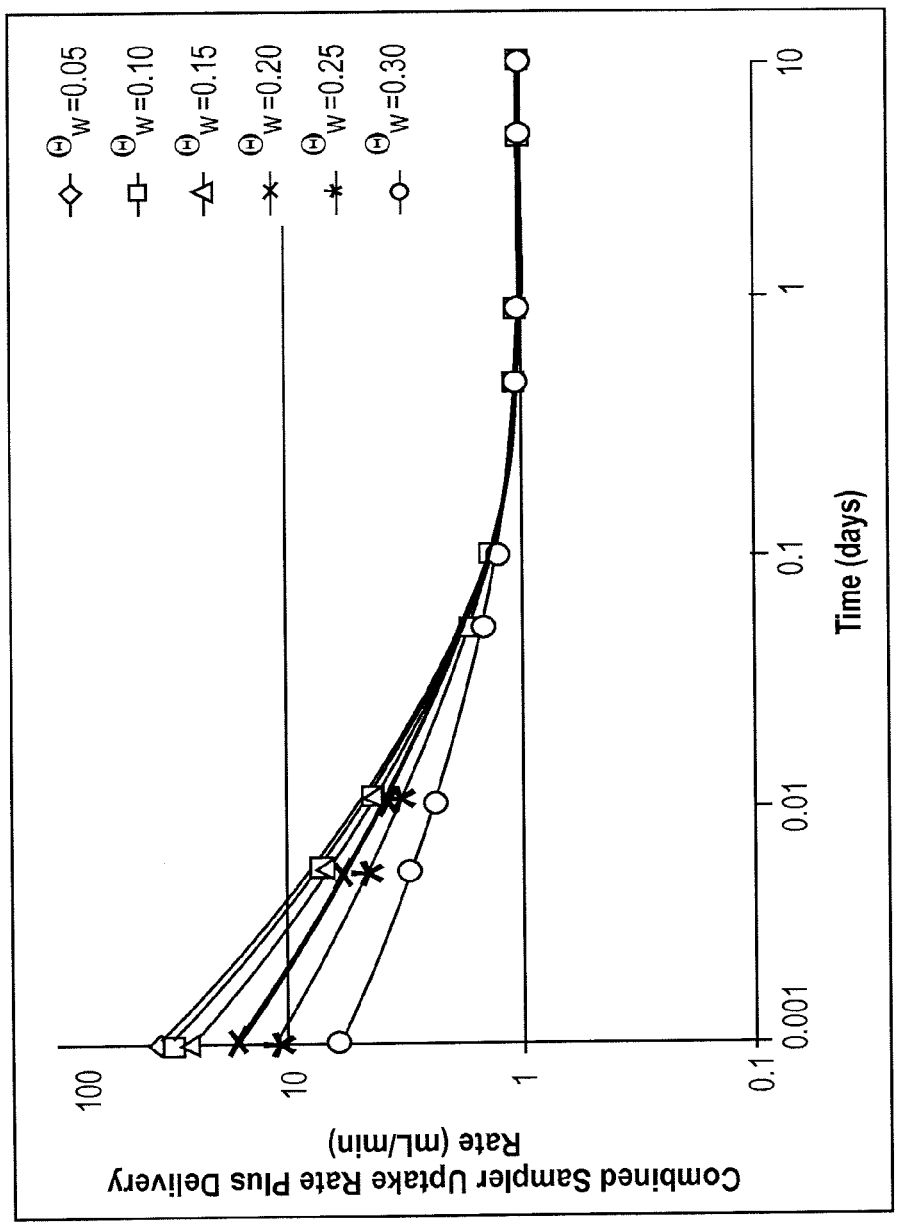
FIG. 6 shows the superimposed diffusive delivery rate of TCE plus uptake rate versus time for a 10 cm tall and 2.5 cm diameter void space in a soil with 37.5% total porosity containing a passive sampler with an uptake rate of 1 mL/min at various levels of water-filled porosity.

The transient mathematical model presented in the previous section is only part of the process, and the uptake rate by the sampler is also important to consider. A transient mathematical model including 2-dimensional radial diffusion to the void space (diffusive delivery), 3-dimensional diffusion through the void-space to the passive sampler and uptake by the sampler is challenging to simulate mathematically. However, an approximate model can be derived by adding the diffusive delivery rate (FIG. 4) and the sampler uptake rate to estimate the effect of both processes occurring at the same time. This is an approximation; however, as long as the uptake rate of the sampler is lower than the diffusive delivery rate to the void space, the combined model will only be different than the analytical model of radial diffusion after the diffusion into the void space has very nearly attained steady-state, at which time the diffusive delivery rate of vapors into the void space will stabilize at the same value as the uptake rate of the sampler. FIG. 6 shows an example of the diffusive uptake rate that would be expected if a passive sampler with an uptake rate of 1 mL/min was placed in the void-space simulated in FIG. 5. Within about one day, the delivery rate for all water-filled porosities approaches the uptake rate of the sampler. More specifically, FIG. 6 shows that a steady-state condition would be achieved in a day or less for all water contents and this condition would be approached (within a factor of two) within an hour or less.

It should be noted that for very wet soils (water-filled porosity greater than 0.25), the steady-state delivery rate may be less than 1 mL/min, in which case there are two possibilities: 1) a lower uptake rate sampler could be used, or 2) a negative bias attributable to starvation may still be experienced. If the negative bias is predictable or acceptably small, the data may still be useful and this may be reasonably evaluated using the models presented here as long as the porosity and moisture content are known or can be reasonably estimated.

Steady-State Model

If the duration of passive sampling is long compared to the time required for the vapor concentrations in the void space to approach equilibrium with the surrounding soils, then a steady-state model would also provide insight into the passive sampling mechanisms. For this case, the conceptual model is as follows:

The vapor concentration in the soil surrounding the void space is uniform at $C_{sg}$ beyond a radial distance of $r_3$ (some distance beyond the radius of the borehole, where soil vapor concentrations are unaffected by the borehole or passive sampler), Diffusion occurs in the region between the outer wall of the drill-hole (radius=$r_2$) and $r_3$, through a cylinder of height, h, The concentration inside the void space of the borehole ($C_{bh}$) is lower than $C_{sg}$ by a factor $\delta = C_{bh}/C_{sg}$, Radial diffusion occurs from the soil to the void space at a diffusion delivery rate equal to the passive sampler uptake rate for the majority of the sample deployment period.

The rate of mass transfer of vapors into the borehole via vapor diffusion through the surrounding soil (M1) is given by H. S. Carslaw and H. C. Jaeger (1959);

$$M1 = \frac{2\pi h D_{eff}(C_{sg} - C_{bh})}{\ln\left(\frac{r_3}{r_2}\right)} \quad (4)$$

The rate of mass uptake by sampler (M2) is given by:

$$M2 = C_{bh} \times UR \quad (5)$$

Setting M1=M2 gives:

$$UR\left[\frac{mL}{min}\right] = \frac{2\pi h[cm]D_{eff}\left[\frac{cm^2}{z}\right](1-\delta)}{\ln\left(\frac{r_3}{r_2}\right)\delta} \times 60 \text{ [s/min]} \qquad (6)$$

Figure 7:
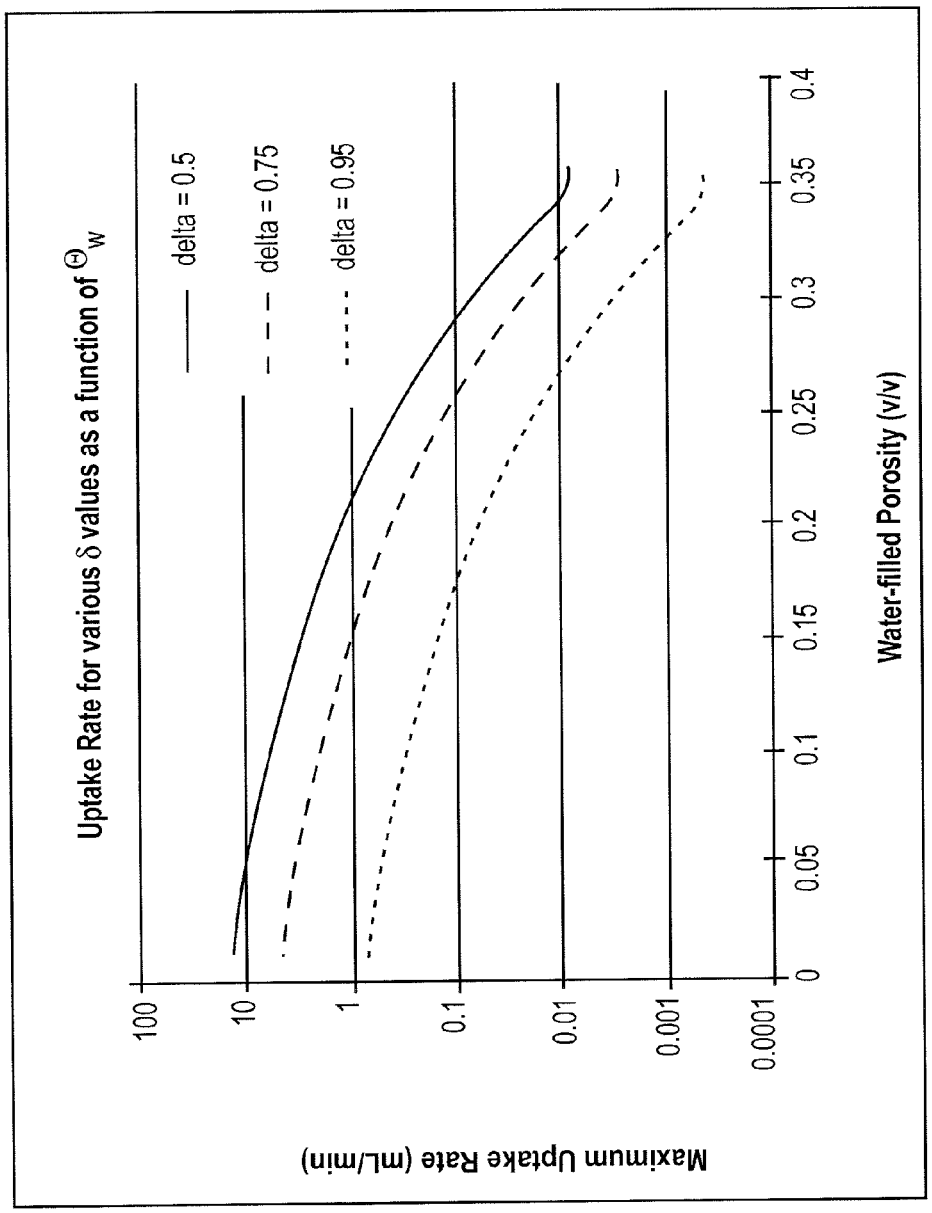
FIG. 7 depicts the diffusive delivery rate calculated using the steady-state model corresponding to various $\delta$ values as a function of water-filled porosity for a 10 cm tall and 2.5 cm diameter void-space assuming $r_3=1$ m.
Figure 8:
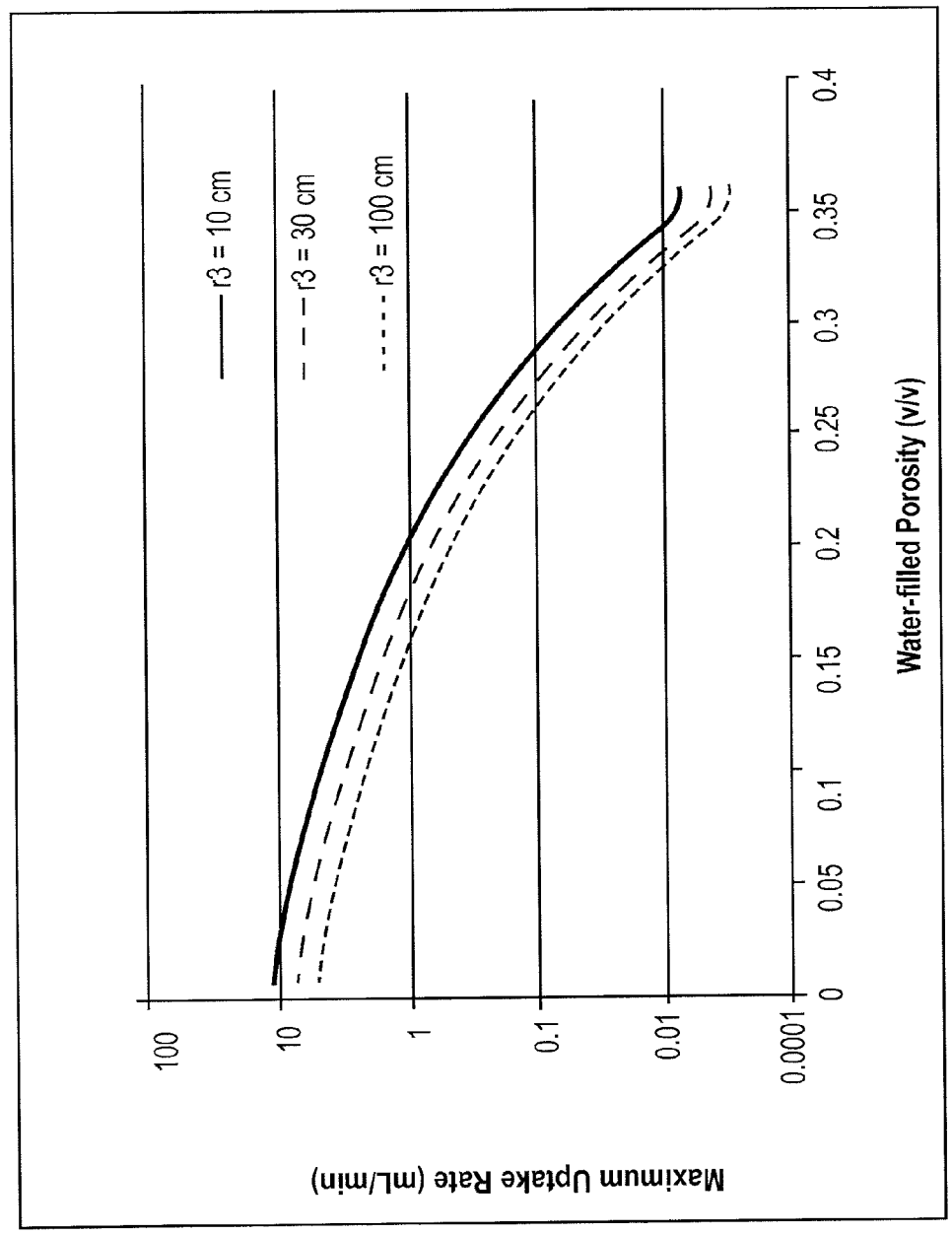
FIG. 8 shows the diffusive delivery rate calculated using the steady-state model corresponding to various $r_3$ values as a function of water-filled porosity for a 10 cm tall and 2.5 cm diameter void-space assuming $\delta=0.75$.

If a passive sampler is deployed in a nominal 1-inch diameter borehole ($r_2$=1.25 cm) and sealed within a 10 cm void space (h=10 cm), the uptake rates as a function of water-filled porosity calculated using equation 6 are shown in FIG. 7. FIG. 7 depicts the diffusive delivery rate calculated using the steady-state model corresponding δ values of 0.5, 0.75 and 0.95 as a function of water-filled porosity for a 10 cm tall and 2.5 cm diameter void-space assuming $r_3$=1 m, where δ is the ratio of the vapor concentration in the void-space divided by the vapor concentration in the surrounding soil and $r_3$ is the radius beyond which the soil vapor concentrations are unaffected by the borehole or sampler. FIG. 7 shows that an uptake rate of 10 mL/min might be acceptable for very dry soil if the data quality objective was to quantify concentrations within a factor of two (i.e., δ=0.5), however; an uptake rate of 1 mL/min would be more suitable for soils with up to 40% water saturation (water-filled porosity of 15% in a soil with total porosity of 37.5%), assuming a more stringent data quality objective of +/−25% (i.e., δ=0.75). Progressively lower uptake rates would be required to further reduce the negative bias or meet typical data quality objectives in very wet soils. For example, a sampler with an uptake rate of 0.1 mL/min would only cause a 50% reduction in the vapor concentrations in the void-space for soils with a water-filled porosity of up to 30%. FIGS. 7 and 8 relate to the steady-state model.

A sensitivity analysis on the $r_3$ value is shown in FIG. 8 for the same conditions as in FIG. 7 and a δ value of 0.75. FIG. 8 shows the calculated uptake rate corresponding to various $r_3$ values ($r_3$ is the distance beyond which soil vapor concentrations are unaffected by the borehole and passive sampler) as a function of water-filled porosity for a 1-inch diameter drill-hole assuming δ=0.75. FIG. 8 shows that the model results are relatively insensitive to the value selected for $r_3$.

Sensitivity Considerations

There is a practical lower limit to the uptake rate for passive sampling imposed by the exposure duration (or sampling time period) needed to achieve a specified concentration reporting limit. Equation (1) can be rearranged to calculate the exposure duration (t) required to achieve a target reporting limit ($C_o$) if the uptake rate (UR), and the laboratory mass reporting limit ($M_{RL}$) are known:

$$t = \frac{M_{RL}}{C_o \times UR} \qquad (7)$$

For example, consider an initial soil vapor concentration of 100 μg/m³ of TCE and a sampler with an uptake rate of 1 mL/minute. A detectable mass of TCE (approximately 0.05 μg via solvent extraction, GC/MS) would be sorbed by the sampler in less than a day. This demonstrates that a low-uptake rate sampler can provide practical sensitivity within a reasonable amount of time and still avoid or minimize the starvation effect. However, if the uptake rate was reduced to 0.1 or 0.01 mL/min, the exposure duration would need to increase proportionately, and there are logistical challenges with exposure durations of 10 to 100 days (costs of return travel to field sites, security over longer deployments, etc.). The minimum detectable mass can be reduced if needed using thermal desorption instead of solvent extraction as the laboratory sample preparation method, so the invention allows for both options. Thermal desorption allows the minimal detectable mass to be much lower (about 0.001 μg), which would provide the same sensitivity (concentration reporting limit) with the same sampling time for an uptake rate of 50 times lower than a sampler using solvent extraction.

Summary of Mathematical Model Simulations

In order for a kinetic passive sampler to provide quantitative soil vapor concentration data, it must have a known and reliable uptake rate for all of the compounds of interest. In order to minimize the starvation effect, the passive sampler uptake rate should be lower than the rate of diffusive delivery of vapors into the void space from the surrounding soil. In order to provide good sensitivity (ability to detect low concentrations) without an excessive sampling period, it is also important that the sampler uptake rate not be unnecessarily low. An uptake rate in the range of about 0.1 to 10 mL/min may be suitable, depending on the soil moisture content, and uptake rates in the range of about 0.1 to 1 mL/min are likely to be suitable over a practicably wide range of moisture contents typically found in unsaturated soils.

Sampling Device

Figure 9:
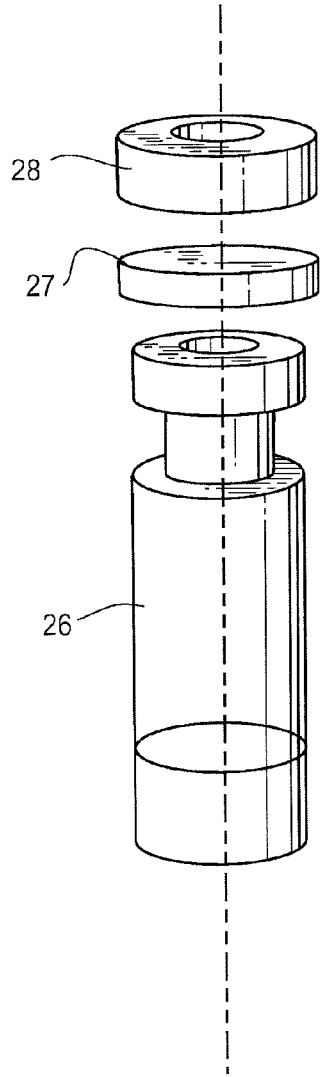
FIG. 9 depicts a disposable passive sampler, according to an illustrative embodiment of the invention.
Figure 10:
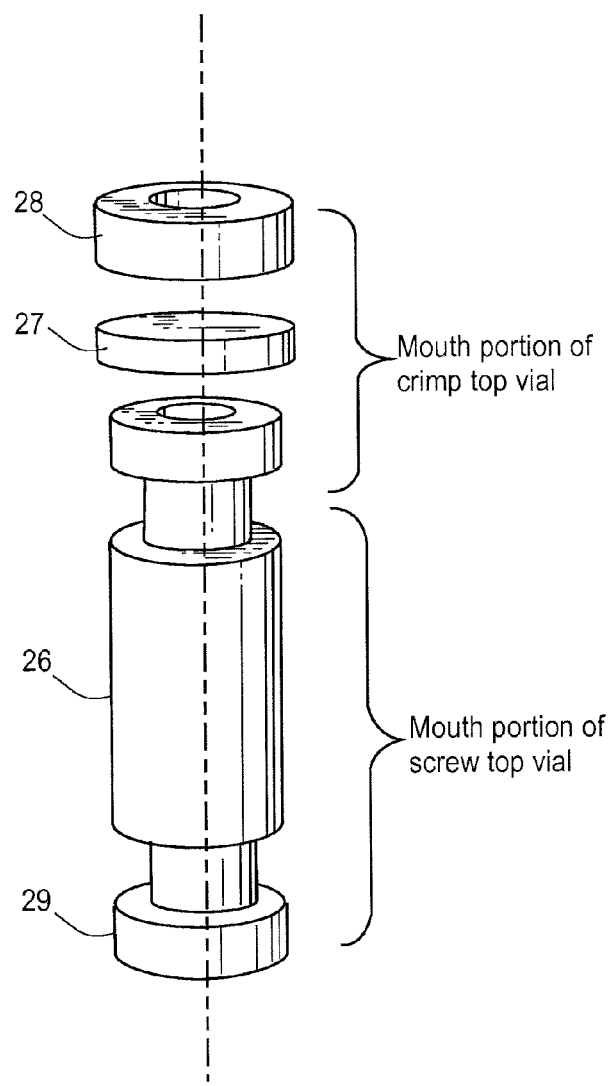
FIG. 10 depicts a reusable passive sampler, according to an illustrative embodiment of the invention.

FIGS. 9, 10 show samplers according to illustrative embodiments of the invention. FIG. 9 depicts a disposable sampler and FIG. 10 depicts a reusable sampler. The sampler comprises a container 26 (for example, approximately 0.8 mL glass vial, or equivalent) filled with a sorbent medium (e.g. Anasorb 747, or one or more of several other suitable media), and the opening of the container is covered with a thin film membrane 27 with a uniform thickness, for example polydimethylsiloxane (PDMS). In this embodiment, membrane 27 is used to seal the container (for example, using an aluminum crimp cap 28). The reusable sampler employs a screw cap 29, preferably of plastic, at the bottom of container 26, to facilitate cleaning so it can be reused. The device is designed to optimize the uptake rate to within a range of values calculated mathematically to minimize or eliminate the starvation effect for most soil types and provide acceptable sensitivity with a practical sample period. The membrane thickness can be adjusted to manipulate the uptake rate depending on the requirements. For example, thicknesses from about 25 μm to about 150 μm may be used. Additionally, or instead, the vial dimensions, in particular the area of the vial opening, may be varied, as the opening itself affects the uptake rate. The opening area may include a single hole or a plurality of holes. As an example, vials of 1.8 mL and 0.8 mL may be used, which will vary in opening size. For a specific vial size, PTFE washer pairs can be incorporated to further define the area exposed to the sample.

The passive sampler may be fabricated, according to an illustrative embodiment of the invention, by cutting a membrane to fit the opening of the container (vial); adding sorbent to the container, assembling the membrane and cap and crimping to seal. A support may then be attached to what is the bottom portion of the sampler when filling. The sampler is then turned upside down for lowering into a void space for sampling, such that the sorbent remains in contact with the inner surface of the membrane throughout the sampling period. Alternatively, the amount of sorbent with respect to the size of the vial can be selected to achieve the desired membrane contact. Keeping the sorbent in contact with the inner surface of the membrane during the sampling period preferably maintains a zero-sink condition (vapor concentrations near zero) at the inner surface of the membrane and improves consistency of the concentration gradient that drives the uptake of VOCs into the sampler.

During the exposure period, vapors dissolve into the membrane and permeate across it at rates that are proportional to the linear temperature programmed retention indices (LTPRI) of the compounds of interest in a gas chromatographic column coated with a stationary phase of the same material as the membrane of the sampler (e.g., PDMS, or similar material).

The rate of permeation of a gas across a fluid membrane is 1) proportional to the difference in the concentration of the analyte on the surface on either side of the membrane; 2) proportional to the cross section of the membrane; and 3) inversely proportional to the thickness of the membrane. The following equations apply:

$$\left(\frac{M}{t}\right) = D \frac{A}{L_m} (C_{ma} - C_{ms})$$

$$C_{ma} = KC_a$$

$$\left(\frac{M}{t}\right) = (DK) \frac{A}{L_m} C_0$$

$$k = \frac{L_m}{PA} \qquad C_0 = \frac{kM}{t}$$

Wherein:
M=Amount of analyte collected by the sorbent
D=Diffusion coefficient of the analytes in the membrane (increases with temperature)
A=Area of membrane
$C_{ms}$=Concentration of the analyte "on" the membrane surface in contact with the sorbent.
$C_{ma}$=Concentration of the analyte "on" the membrane surface exposed to air or gas.
t=Sampling time
$L_m$=Membrane thickness
K=Partition coefficient of the analyte between air and the membrane (decreases with temperature)
P=Permeability constant of the polymer towards the analyte (P=D×K)
Co=Concentration of the analyte in air
k=Calibration Constant (time/volume)
$k^{-1}$=Uptake rate (volume/time) (the inverse of the calibration constant)

The uptake rate may be varied by adjusting the area or thickness of the membrane. A combination of the two adjustments can also be made to achieve the desired uptake rate.

The linear temperature-programmed retention index (LTPRI) for VOCs in a chromatographic column with a coating substantially similar to the material used to make the membrane of the sampler (e.g., PDMS) correlates to the calibration constant as follows:

$$\left. \begin{array}{c} LTPRI \propto \ln K \\ \frac{1}{k} = \frac{DK_pA}{L_m} \end{array} \right\} \ln k \propto -LTPRI$$

The LTPRI—Calibration Constant correlation is useful when the identity of the pollutant is unknown at the time of sampling because it allows the uptake rate to be calculated with reasonable accuracy for those compounds for which the uptake rate has not been experimentally measured in controlled laboratory chamber experiments. The correlation also provides the possibility of estimating total petroleum hydrocarbons, which is not possible with other diffusive samplers.

The membrane is hydrophobic (for PDMS, the uptake rate for water is about 60 times lower than the uptake rate for toluene), which reduces the risk of analytical interferences attributable to excessive moisture. Existing tube samplers do not inhibit the entry of water vapor, and therefore, are subject to potential interferences attributable to water.

Various extraction schemes may be used to process/analyze the sample collected with the passive sampler. In a first illustrative embodiment of the invention, the cap is de-crimped and desorption solvent (for example, carbon disulfide, hexane, etc.) is added to the vial. The vial can then be closed by crimping with an aluminum crimp cap with a Teflon® lined septum. The vial is then shaken. A sub-sample of the desorption solvent can then be introduced directly into a gas chromatograph (GC). In another embodiment, the vial cap is de-crimped and the contents transferred to a 4 mL or other size screw cap vial. Desorption solvent is then added, the vial is capped and the vial is shaken. The extracted solvent is transferred to a 2 mL or other suitable size vial, which is sealed by crimping with an aluminum crimp cap with a Teflon® lined septum. The sample can then be introduced into a GC auto-sampler. If a thermally-desorbable sorbent is used (e.g., Tenax TA, Carbopack B, Carboxen 1016 or similar), the sorbent can be transferred from the WMS-LU sampler to an Automated Thermal Desorption (ATD) tube prior to analysis. The mass of each compound is determined using routine gas chromatography with mass spectroscopy or similar laboratory analysis methods.

Illustrative sampling methods for using the passive sampler to measure concentrations of volatile organic compounds in soil gas will now be discussed.

Sampler Activation and Deployment

The sampler is activated (i.e., begins to sorb chemicals from its surrounding) as soon as it is removed from the polycoated aluminum pouch in which it may be stored and the 20 mL glass overpack vial which may be used to protect the sampler from exposure to chemicals during shipment. It is preferable to minimize the above-ground exposure time to avoid potential interferences from background sources of volatile organic compounds when the objective is to measure subsurface vapor concentrations.

During the deployment period, the sampler should be positioned such that the sorbent inside the vial is in direct contact with the membrane.

Sampler Retrieval

The sampler is deactivated by returning it (including the plastic holder, if used) into the 20 mL glass overpack vial, or other suitable protective packaging. The overpack vial can be sealed, for example by screwing the cap tightly onto the overpack vial and putting Teflon® tape around the outside of the cap/vial junction. The sampler is now deactivated.

Illustrative methods involve exposing the sampler to a void space in the subsurface through a hole drilled to a specified target depth.

The sampler is lowered into the borehole and the sampler is either wrapped with aluminum insect mesh or a coil of stainless steel wire, or other component of suitable material, to protect the membrane from contacting soil surfaces during deployment and retrieval.

The borehole should be sealed after deployment of the sampler to prevent atmospheric air leakage into the borehole or losses of VOC to the atmosphere during the sampling period. Sampling can be accomplished in a variety of ways, including the three ways, described below:

1) Deployment in a Semi-Permanent Passive Soil Vapor Monitoring Probe:

If the geologic materials are not cohesive and there is a risk the borehole will collapse, or if periodic monitoring is planned using reproducible sampling conditions, or if the depth of deployment is greater than about 3 m, it may be preferable to install a semi-permanent passive soil vapor monitoring probe.

Two features are preferred for the passive soil gas probe: 1) a rigid, inert pipe should be suspended above the bottom of the borehole, so the lowest part of the borehole allows open communication between the surrounding soil and the open void space in which the sampler will be deployed, and 2) the annulus between the pipe and the borehole wall must be sealed in such a way as to prevent air flow and prevent the seal from filling the void space at the bottom of the pipe. The diameter of the pipe must be large enough to accommodate the sampler (e.g., about 1 or 2 inch).

Figure 11:
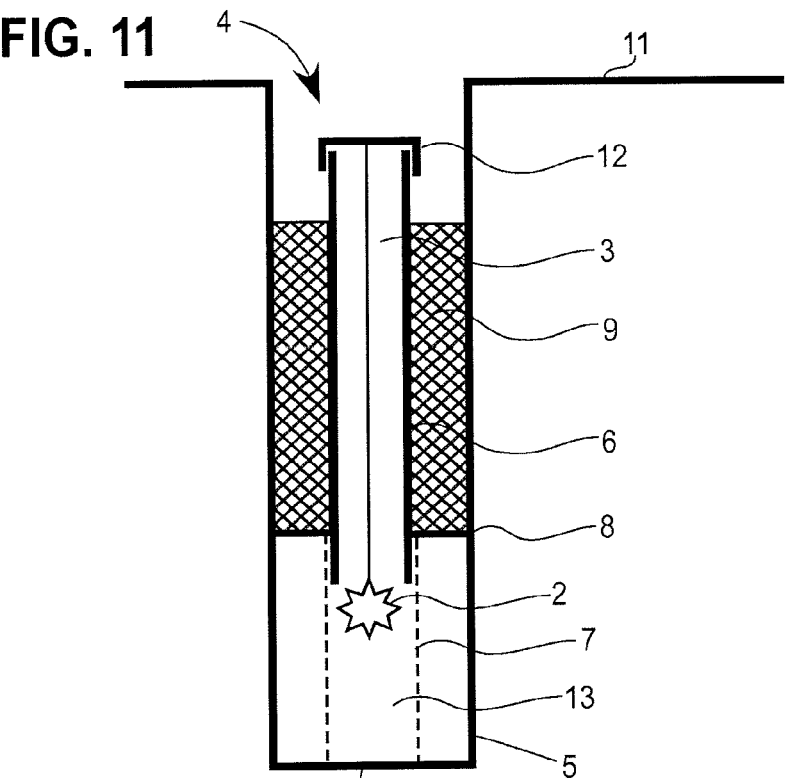
FIG. 11 is a schematic diagram of a first option for semi-permanent probes for passive soil vapor sampling, according to an illustrative embodiment of the invention.
Figure 12:
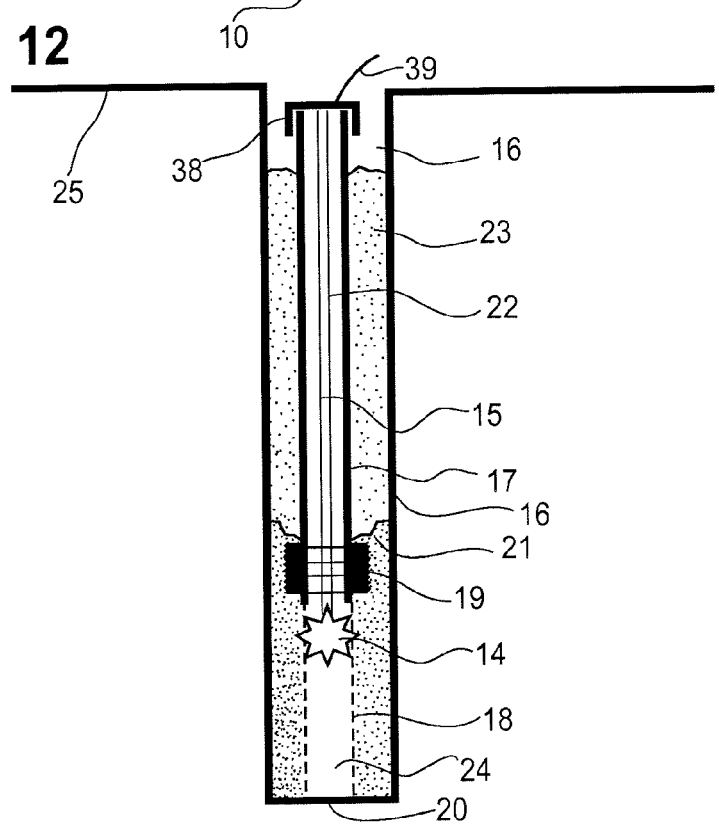
FIG. 12 is a second option for semi-permanent probes for passive soil vapor sampling, according to an illustrative embodiment of the invention.

FIGS. 11 and 12 are schematic diagrams of two options for semi-permanent probes for passive soil vapor sampling according to an illustrative embodiment of the invention. In FIG. 11, a passive sampler 2 extending from a nylon line 3 is deployed in a borehole 4 having walls 5. A 2-in (or other suitable size) inert pipe 6 is disposed within borehole 4, and is supported by stilts 7. The pipe may be made of any inert, rigid material (for example, of PVC). A gasket 8 surrounds pipe 6 toward the pipe's lower end, which in this example is approximately 2 feet from the borehole bottom 10 and approximately 10 feet below ground surface 11 (these dimensions can be varied as appropriate for a specific vertical discretization of soil vapor concentration monitoring). Space between borehole wall 5 and pipe 6 is filled with a material such as bentonite slurry to form an annular seal 9. A slip cap 12 closes the space in which passive sampler 2 is deployed. Alternatively, a deeper seal could be placed using the same method for temporary holes that is described below. The void space is designated by reference number 13.

FIG. 12 is a similar schematic diagram of a semi-permanent probe for passive soil vapor sampling according to an illustrative embodiment of the invention, with a slightly different option for the annular seal and two holes through a slip-cap 38 having a purge line 39 for purging and collection of active samples within borehole 16, if needed or desired. A passive sampler 14 extending from a nylon line 15 is deployed in a 4-in (or other suitable size) auger hole 16. A 2-in (or other suitable size) PVC pipe 17 is supported by stilts 18. A stainless steel ring clamp 19 is positioned at the lower end of pipe 17 to fasten the plastic sleeve 21 and stilts 18 to the pipe, in this example at about 6-18 inches (or other dimensions as needed to suit site-specific conditions and objectives) above the borehole bottom 20. A plastic sleeve 21 with a diameter larger than the borehole wall is disposed within borehole 16 and surrounding the pipe 17. Within pipe 17 is a ⅛-in stainless steel drop tube 22. Pipe 17 extends to approximately 3 ft from ground surface 25 in this example, but this can be varied a needed. Compacted sand 23 fills the space between the plastic sleeve 21 and the outside surface of pipe 17 to form a seal between the pipe and the borehole wall. Passive sampler 14 is shown extended to void space 24.

Figure 13A:
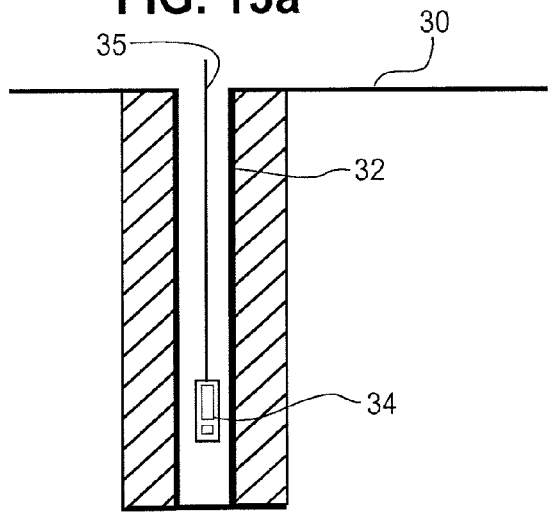
FIGS. 13a-c depict a method of sampling in a temporary (uncased) hole, according to an illustrative embodiment of the invention.
Figure 13B:
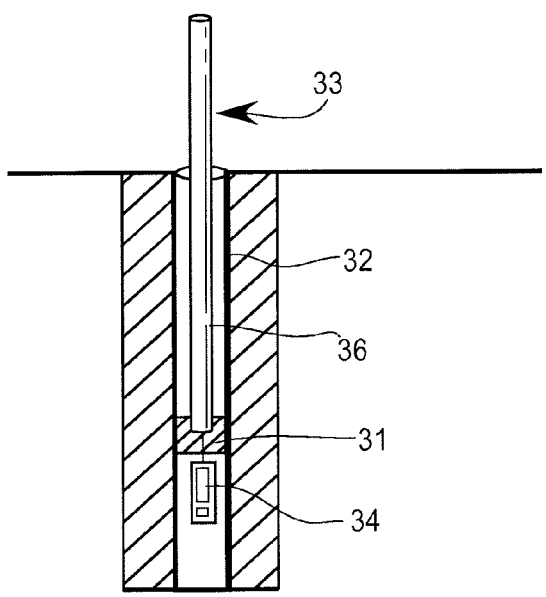
Figure 13C:
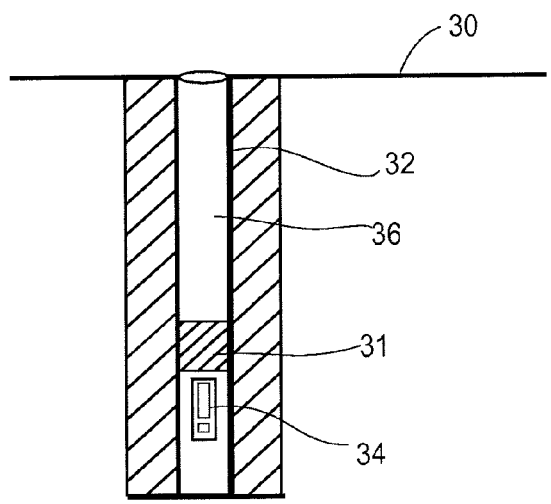

2) Deployment in an Open Hole:

If the geologic materials are cohesive enough to stand open, and the sampling depth is about 3 m or less, an open hole may be used for deployment. After placement of the sampler, the hole may be sealed a short distance above the sampler using a flexible and relatively inert plastic sleeve (e.g., polyethylene or ethyl vinyl alcohol) of a diameter slightly larger than the borehole with a plug inside the plastic sleeve of foam rubber or similar compressible material to press the sleeve against the wall of the borehole with sufficient force to form a seal, but with a pressure small enough that the seal can easily be removed by pulling up on the sleeve at the end of the sampling period. This kind of seal could also be used in a semi-permanent probe, if desired. According to an illustrative embodiment of the invention, such a seal may be placed as shown in FIGS. 13a-c by taking the following steps:

a) Cut the plastic sleeve 36 to a length of about 30 cm longer than the depth from ground surface 30 to which the seal is desired. Close the bottom of the sleeve, for example, by folding and stapling the bottom closed or by heat-sealing, as desired;

b) Compress a foam plug 31 and place it inside one end of a thin-walled rigid pipe (plastic or metal) slightly smaller in diameter than a drilled hole 32. Place a dowel 33 of smaller diameter than the pipe inside the pipe, and place the pipe inside the plastic sleeve;

c) Drill the borehole 32 and remove soil. Promptly lower a sampler 34 to the target depth, and secure the retrieval tether (nylon line or stainless steel wire for example) 35 at ground surface 30;

d) Lower the plastic sleeve, pipe and dowel to a depth slightly above the passive sampler 34 as shown in FIG. 13b.

e) Hold the dowel stationary and lift on the pipe until the dowel extends below the bottom of the pipe, which will force the foam out of the pipe and allow it to expand, pressing the sleeve against borehole 32 wall and forming a seal 36 just above the passive sampler as shown in FIG. 11c.

f) Seal 36 remains in place for the duration of the sample deployment, at which point the plastic sleeve is retrieved from borehole 32.

g) Retrieve passive sampler 34 after seal 36 is removed. Plug the borehole, such as with a cement/bentonite grout or according to local regulations.

The plastic sleeve is preferably made of an inert and flexible material. Examples of materials include, but are not limited to, high density polyethylene, ethyl vinyl alcohol, or fluoropolymers such as Teflon®. A combination of aluminum foil with other materials could also be used to form a more inert seal, if needed (e.g., if the target chemicals are strongly sorbed by plastics).

The method shown in FIGS. 13a-c can be used in either a temporary borehole with no casing or in a semi-permanent probe with casing 3) Sub-Slab Sampling:

For sampling below concrete floor slabs the sampling protocol is, for example:

a) Prepare the sampler to protect the membrane from contact with the soil;

b) Drill a hole through the floor;

c) Lower the sampler into the hole through the floor;

d) Seal the hole with an inert, removable stopper for the duration of the sampling period;

e) At the end of the sampling period, remove the stopper and the sampler from the hole, and f) seal the hole with grout or other suitable sealant.

Figure 14A:
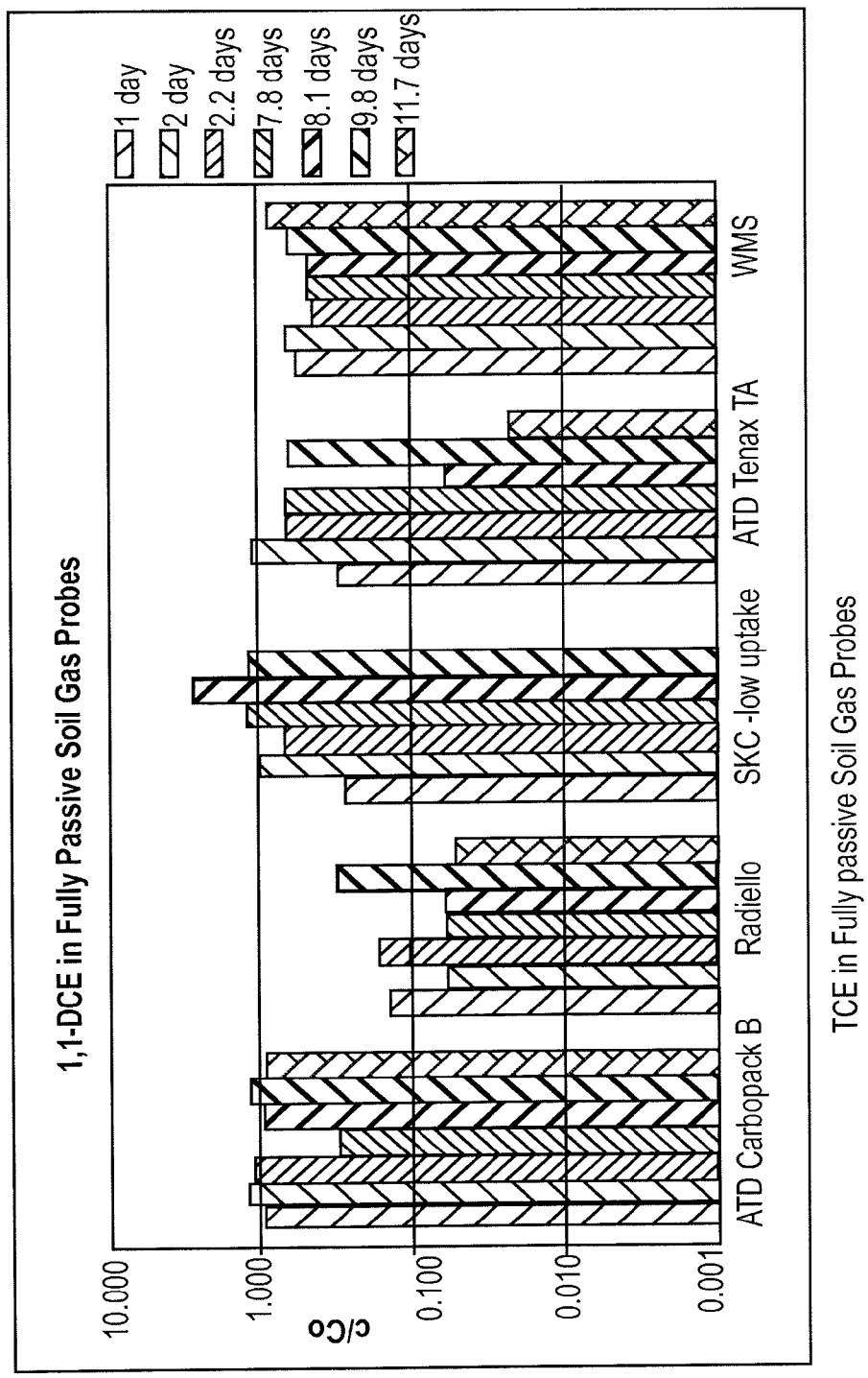
FIGS. 14a,b shows the relative concentration (passive/active, or C/Co) for 1,1-DCE and TCE, respectively, at a field sampling demonstration site with soil gas probes constructed as shown in FIG. 11, including for comparison purposes data from other passive sampling devices.
Figure 14B:
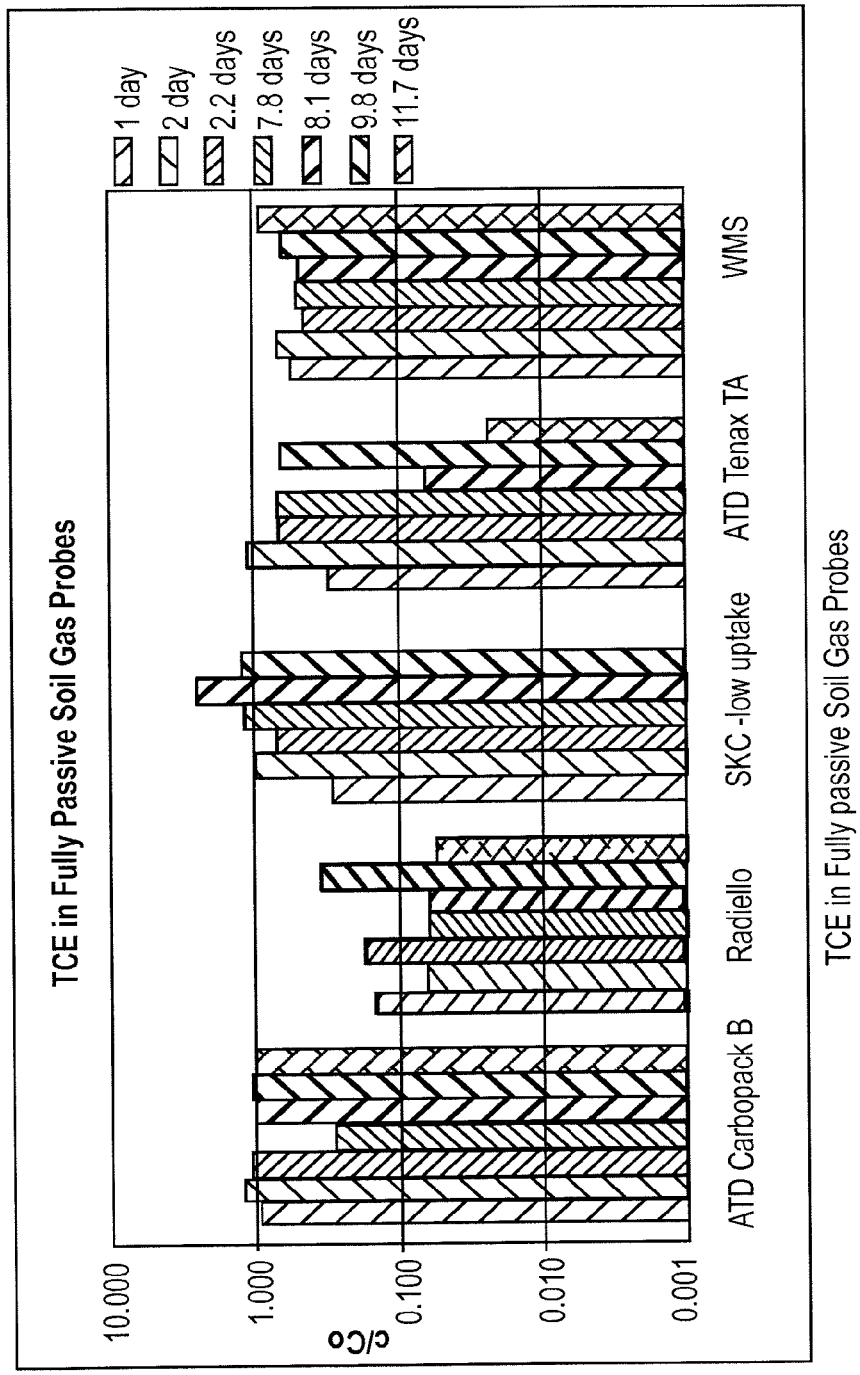
Figure 15A:
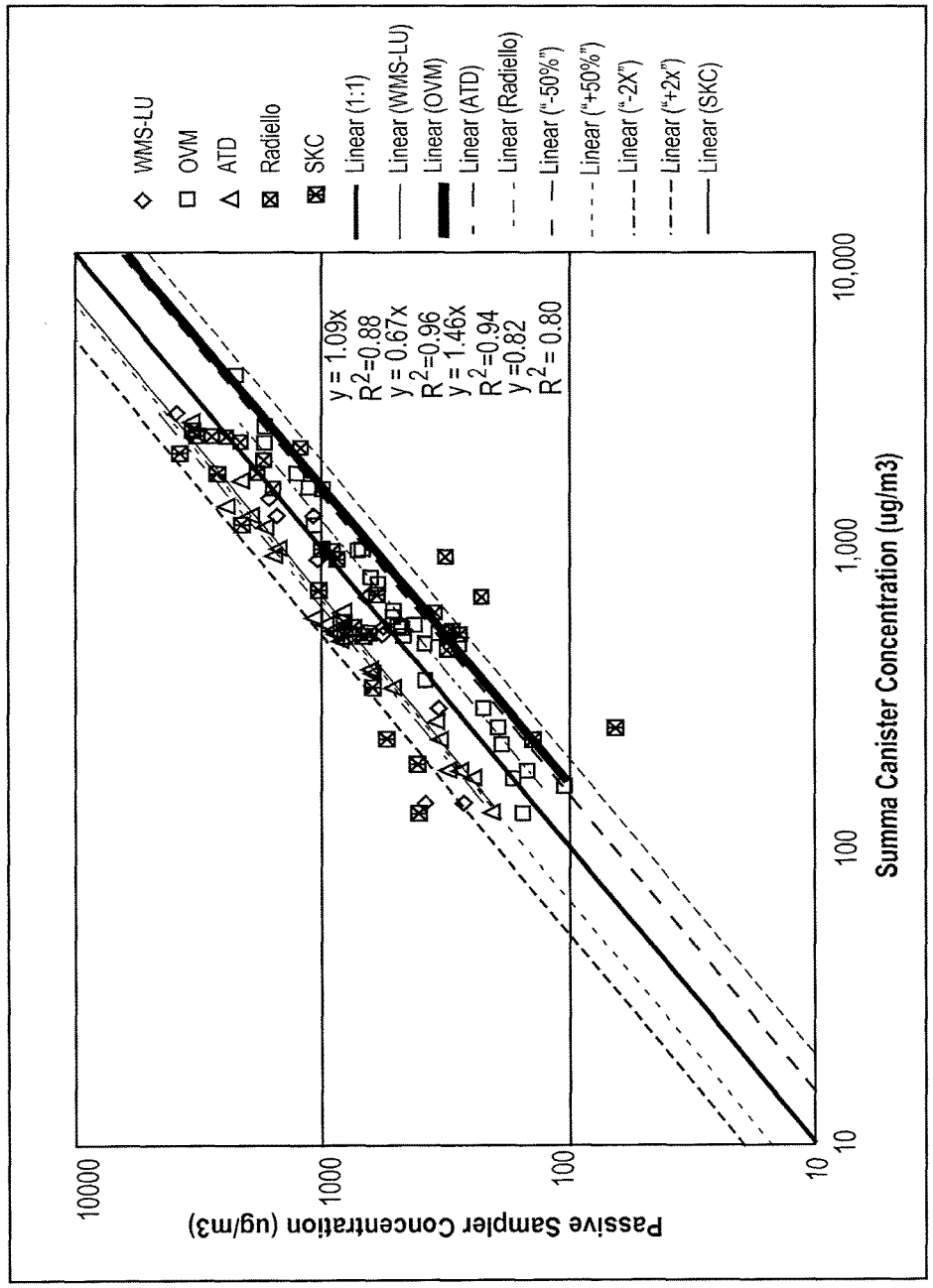
FIGS. 15a,b show the correlation between passive samples and Summa® canister samples at a field sampling demonstration site with soil gas probes constructed as shown in FIG. 12 (for FIG. 15a) or sub-slab probes (for FIG. 15b), with linear regressions and correlation coefficients ($R^2$), including for comparison purposes data from other passive sampling devices.
Figure 15B:
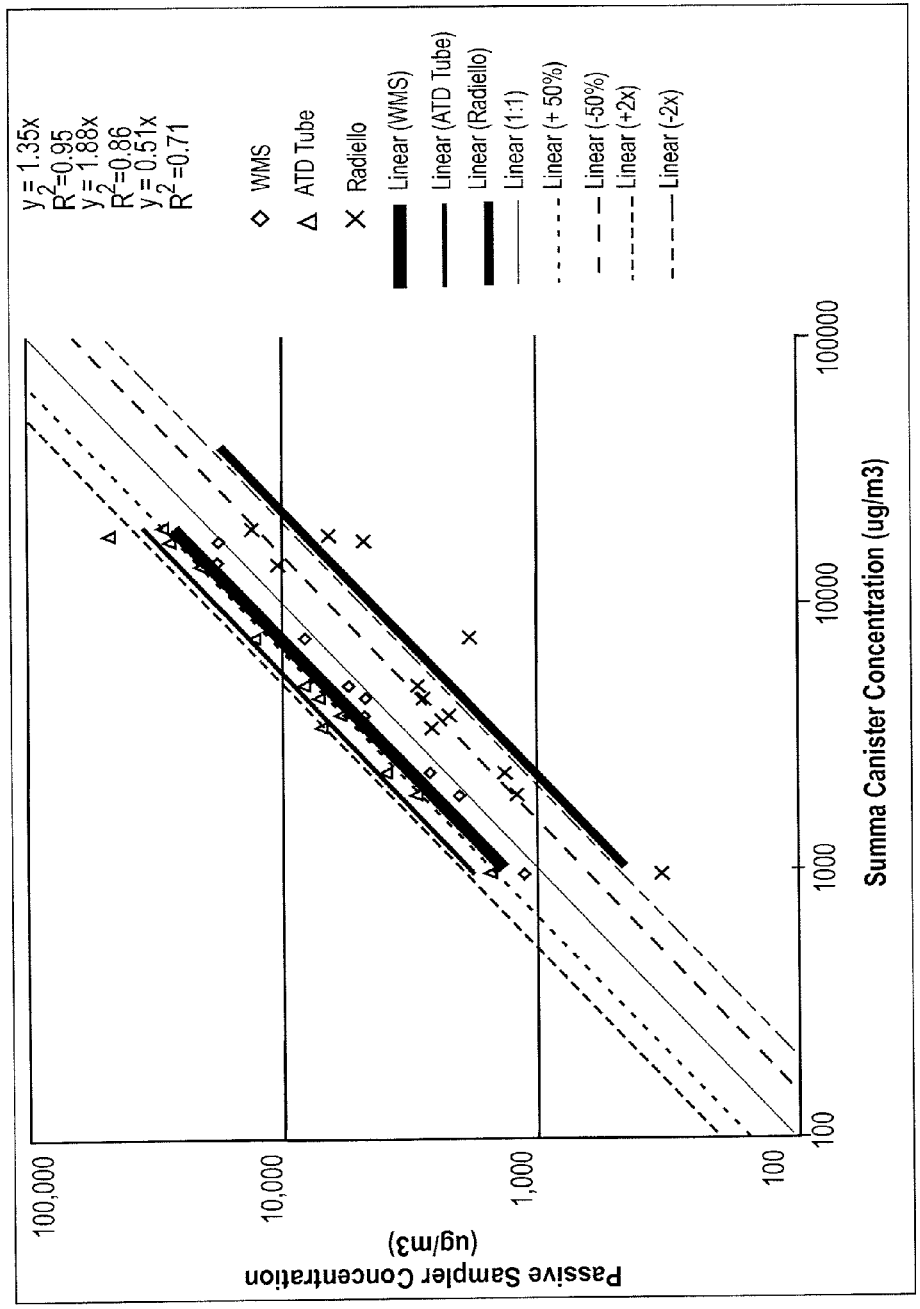

FIGS. 14a,b show relative concentration (passive/active, or C/Co) at a field sampling demonstration site using soil gas probes as shown in FIG. 11 for 1,1-dichloroethene (1,1-DCE) (FIG. 14a) and TCE (FIG. 14b), respectively. FIGS. 14a,b show that a sampler according to an illustrative embodiment of the invention (the WMS sampler) yields relative concentrations (C/Co, where C is the passive sampler concentration and Co is the concentration measured via conventional active sampling) very near the ideal value of 1.0 for both TCE and 1,1-DCE with no notable dependence on the sample duration (from 1 to 11.7 days). Other samplers were included in this experiment (and are also shown of FIGS. 14a,b), which showed either a low bias attributable to the starvation effect, poor retention in longer-term samples, or less consistency than the WMS sampler. FIG. 15a shows the correlation between passive samples and Summa® Canister Samples using probes as shown in FIG. 12, and FIG. 15b shows the correlation between passive samplers and Summa® canister samples using sub-slab probes. Both FIGS. 15a,b include linear regressions and correlation coefficients ($R^2$). FIGS. 15a,b show that the WMS sampler has a better correlation to conventional active soil vapor samples (via Summa canisters) than other samplers tested for soil gas and sub-slab samples over a concentration range of about 100 µg/m³ to over 10,000 µg/m³.

Figure 16:
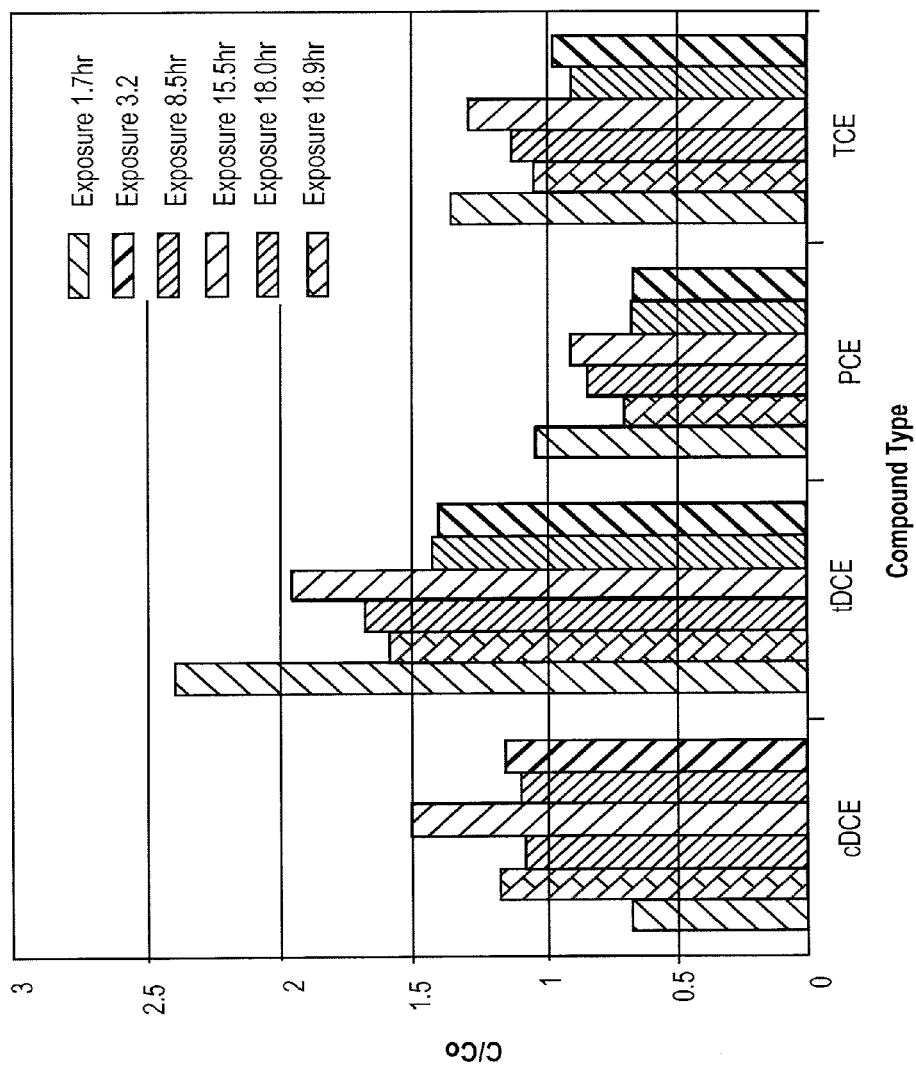
FIG. 16 shows the relative concentration (passive/Summa®) of four different VOCs as a range of different sampling periods for a sampler in a 1-inch (2.54 cm) diameter temporary probe as shown in FIG. 13a-c.

FIG. 16 shows the relative concentration (passive/Summa®) for the WMS/low-uptake sampler in a 1-inch (2.54 cm) diameter open borehole (such as in FIGS. 13a-c) open from 4 to 5 feet below ground surface at a field sampling demonstration site. FIG. 16 shows that the WMS-LU sampler provides reasonably accurate and precise concentrations for tetrachloroethene (PCE), TCE, cis-1,2-dichloroethene (cDCE) and trans-1,2-dichloroethene (tDCE) over durations ranging from 1.7 hours to 18.9 hours.

Figure 17A:
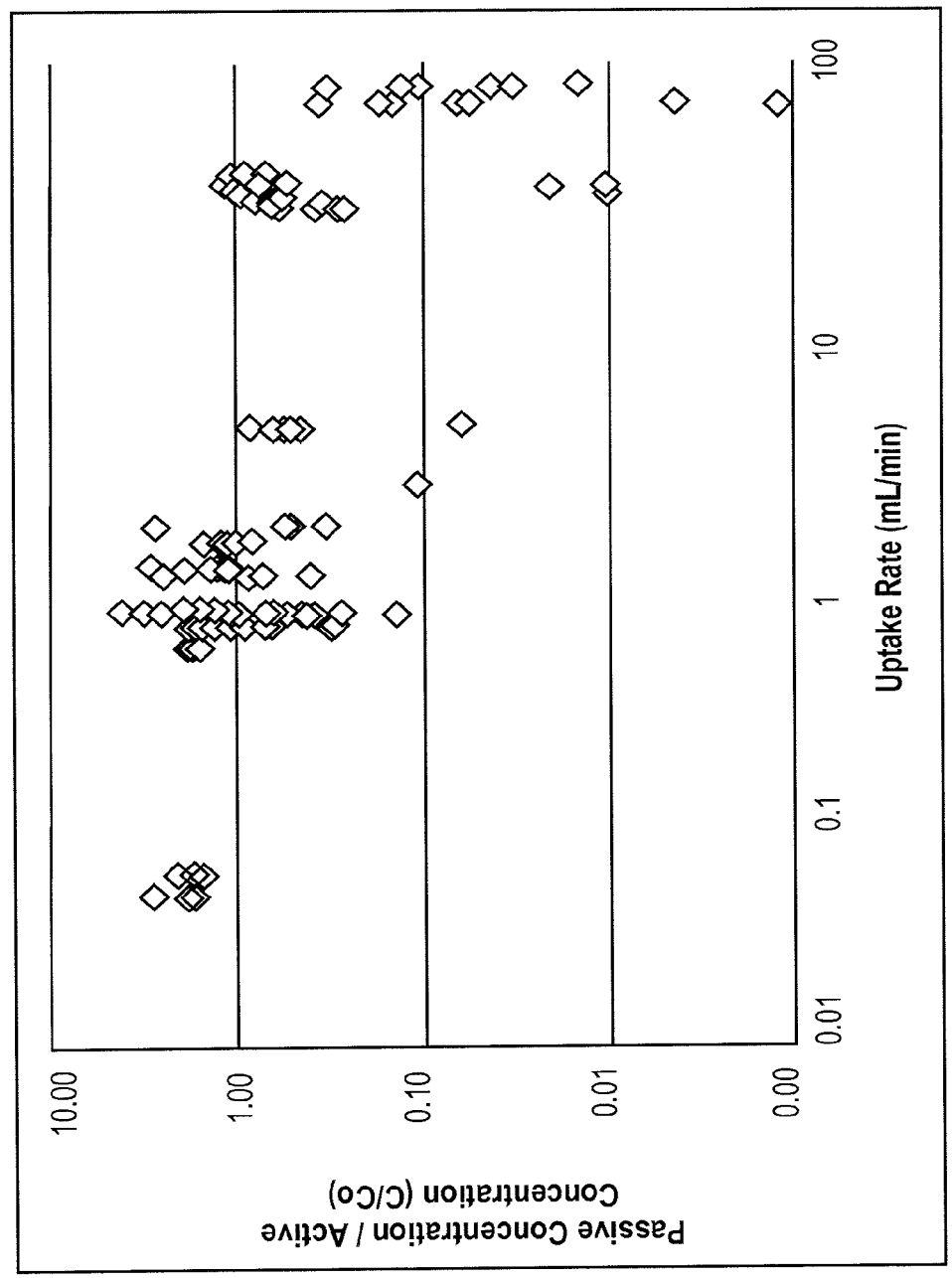
FIGS. 17a,b show the relative concentration ($C_{passive}/C_{active}$) versus (FIG. 17a) uptake rate (UR), and (FIG. 17b) (UR×sample time)/Void Volume.
Figure 17B:
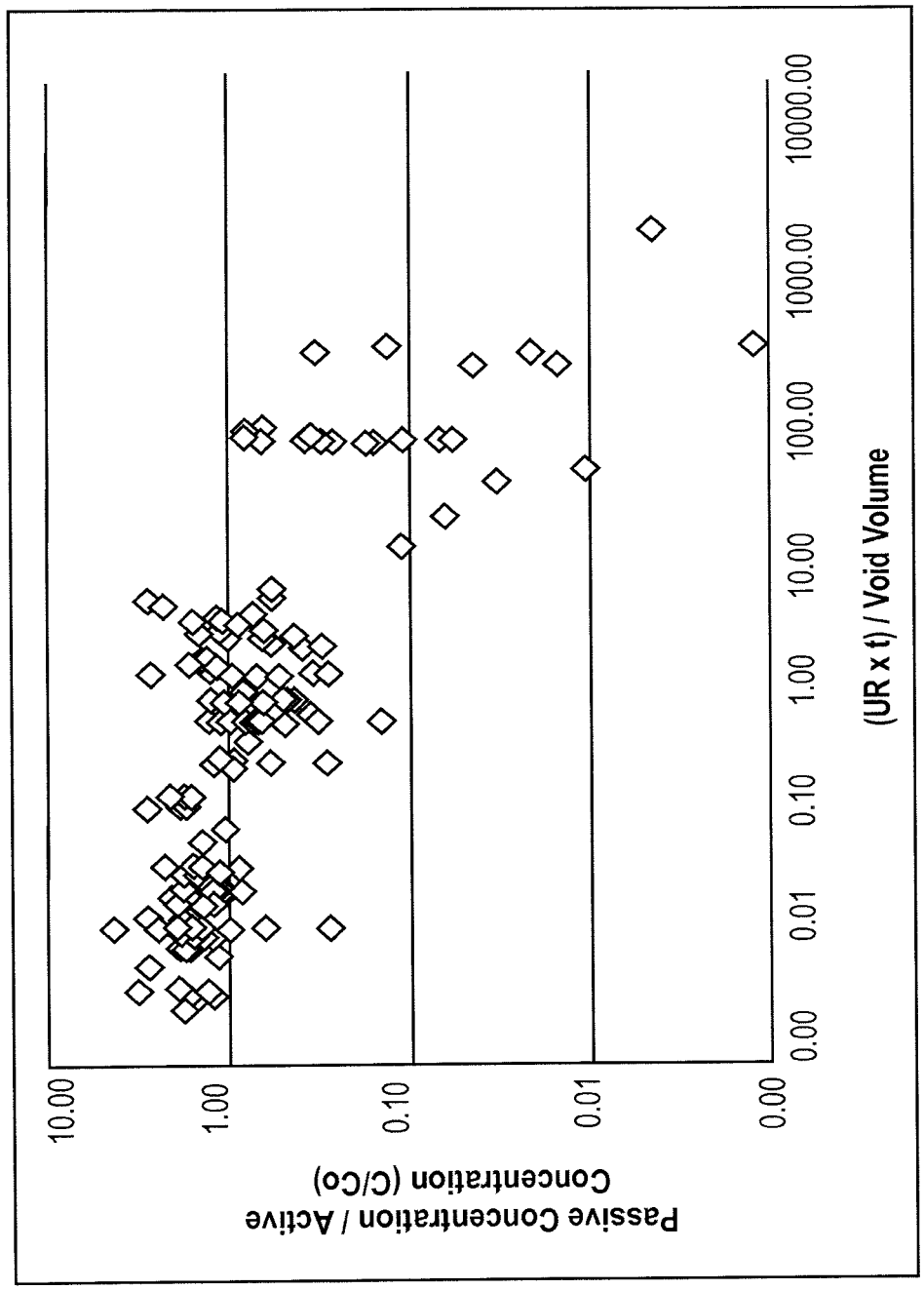

FIGS. 17a,b show relative concentration ($C_{passive}/C_{active}$) versus uptake rate (UR) (FIG. 17a), and (UR×sampling time)/Void Volume (FIG. 17b) for data from controlled field experiments with several different passive sampler types. FIGS. 17a,b show that negative bias from the starvation effect is minimized when the uptake rate is about 1 mL/min or less or when the product of the uptake rate and the sample duration is less than the volume of the void space for probes that are purged at the outset of the sampling period.

Deployment Time

The passive sampler deployment time can be calculated using either the target reporting limit (in areas of low vapor concentrations) or the expected vapor concentration if it is known from previous monitoring events or can be reasonably estimated from the field screening readings. The minimum deployment time can be calculated using the following equation:

$$\text{Deployment time (minutes)} = \frac{\text{Analytical Limit of Quantitation (ng)} \times 1{,}000}{\text{Expected Concentration (µg/m}^3\text{)} \times \text{uptake rate (mL/min)}}$$

If the concentration is not known, or if it is below the limit of detection of the field screening instruments, then the estimated concentration in the equation above can be replaced with a value equal to or less than the risk-based target concentration.

In an exemplary embodiment of the invention, the sampler is smaller (0.8 mL vial) than a prior design of polydimethylsiloxane membrane sampler, which was a 1.8 mL vial. The smaller size vial has a smaller opening, and this reduces the uptake rate to within the optimal range of about 0.1 to 1 milliliter per minute (mL/min). The smaller size (with all else equal) would have a minimum detectable vapor concentration about 5 times higher than the larger size for the same exposure duration. Soil gas risk-based screening levels are not as low as screening levels for indoor air samples, so for the purpose of soil vapor sampling, the low uptake rate is typically not a significant limitation, and adequate sensitivity can still be generally achieved with an exposure duration of one day or less. The sensitivity can also be improved using thermal desorption instead of solvent extraction as the method of sample preparation, which reduces the lowest measurable mass (M) from about 50 nanograms to about 1 nanogram or less. The membrane thickness can be increased to decrease the uptake rate as well, in which case, the 1.8 mL vial size may be used for a low-uptake rate sampler, if and as desired. Other illustrative vial sizes and ranges include: less than 1.8 mL, less than 5.0 mL and approximately 0.8 mL to 2.0 mL. As noted previously, the vial size and hence the membrane area may be selected along with the membrane thickness to achieve the desired uptake rate.

A number of variables will determine the optimum uptake rate. For example, if the soil is dry, the uptake rate can be a little higher and if it is wet, it needs to be lower. So, sampler uptake rates in the range of about 0.01 to about 10 mL/min, for example, can potentially result in relatively unbiased quantitative passive soil vapor sampling, depending on the soil moisture. The soil moisture will not always be known in advance, so a lower uptake rate is generally better (applicable in a wider range of conditions). As noted above, a lower uptake rate typically means the sample will need to be left in the ground longer to get enough analyte mass inside to be detected by the laboratory. If a sampler with an uptake rate of 1 mL/min needs 24 hours, then one with an uptake rate of 0.1 mL/min needs 10 days. Therefore, the sampling time needed to achieve a desired minimum detectable concentration may be a limiting factor. Additionally, each compound has a slightly different uptake rate, so this factor must be considered. Accordingly, 0.1 to 1 mL/min is a "sweet-spot", and will usually be the preferred range, but this is approximate and can differ depending on site-specific variables and objectives. The preferred uptake rate for a particular soil porosity and moisture, particular chemical or suite of chemicals, particular laboratory sample preparation method (solvent extraction or thermal desorption) can be determined using the mathematical methods described herein.

The sampler can be used with sorbents that are designed to perform best with thermal desorption or solvent extraction methods of sample preparation. It can also be made with clear or amber glass vials, plastic or metal containers. The membrane area and thickness can be modified to optimize the uptake rate for specific soils or chemicals. And finally, the exposure time can be adjusted to provide a desired reporting limit.

The sampler can be equipped with additional features aimed at protecting it from direct contact with soil (e.g. a wire mesh wrapping, a cage-like enclosure, etc.) and various types of tethers for retrieval from the subsurface (stainless steel wire, nylon line, etc.).

The reliability, accuracy and precision of passive samplers in general depend on the consistency of the uptake rate. For the sampler, the membrane is preferably manufactured with very tight tolerances on the thickness of the membrane. Furthermore, the diameter of the opening of the vial directly affects the uptake rate. In an exemplary embodiment of the invention, the combination of the diameter and thickness of the membrane achieves a desired target uptake rate range of about 0.1 to 1 mL/min.

Various embodiments of the invention have been described, each having a different combination of elements. The invention is not limited to the specific embodiments disclosed, and may include different combinations of the elements disclosed or omission of some elements and the equivalents of such structures, including those of any prior art embodiments of samplers or sampling methods.

While the invention has been described by illustrative embodiments, additional advantages and modifications will occur to those skilled in the art. Therefore, the invention in its broader aspects is not limited to specific details shown and described herein. Modifications, for example, to the specific structure of the sampler and mathematical models, may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. A passive kinetic sampler for quantitative passive soil vapor concentration measurement comprising: a container filled with a sorbent medium and having one or more openings; wherein the sampler has an uptake rate and sampler dimensions that constrain the uptake rate to match values that minimize or eliminate a starvation effect as calculated via mathematical models; wherein the mathematical models calculate a diffusive delivery rate of vapors to a void space in which the passive sampler is deployed and depend at least in part on soil moisture and porosity; and wherein the uptake rate during a sampling interval, as constrained by the sampler dimensions, is less than or about the delivery rate of vapors from surrounding soil, so the concentration of vapors in the void space within which the sampler is exposed is similar to the concentration of vapors in the surrounding soil gas throughout a majority of the sampling interval, wherein the sampler dimensions include the total area of the one more openings through which the sorbent material is exposed to the void space and the container having a volume in the range of 0.8 to 5.0 mL; and wherein the uptake rate that minimizes the starvation effect is less than the diffusive delivery rate.

2. The sampler of claim 1 wherein the container has a volume of approximately 0.8 to 2.0 mL.

3. The sampler of claim 1 wherein the sampler container is smaller than 1.8 mL.

4. The sampler of claim 1 wherein the sampler container is smaller than about 5.0 mL.

5. The sampler of claim 1 wherein the sorbent medium is suitable to retain and recover the target analytes consisting of a method selected from solvent extraction and thermal desorption.

6. The sampler of claim 1 wherein the uptake rate is within the range of about 0.1 to 1 milliliter per minute (mL/min).

7. The sampler of claim 1 wherein the uptake rate is within the range of about 0.01 to about 10 milliliter per minute (mL/min).

8. The sampler of claim 1 wherein the area of opening optimizes the uptake rate for specific chemicals.

9. A method to quantitatively calculate concentrations of volatile organic compound (VOC) vapors below the ground surface comprising:
providing a passive sampler according to claim 1,
allowing the sample to sorb or trap VOC vapors at known uptake rates (UR),
calculating the concentration (C) from a mass (M) of each compound sorbed or trapped and an exposure time (t) of the sample using the following equation:

$$C = \frac{M}{UR \times t}.$$

10. The method of claim 9 wherein the mathematical models include a steady-state and transient mathematical model employing an effective diffusion coefficient derived at least in part from the soil moisture and porosity.

11. The method of claim 9 using either thermal desorption or solvent extraction as a method of sample preparation and selecting sorbents depending on the sample preparation method used.

12. The method of claim 9 wherein the sampler dimensions include the area of the openings through which the sorbent material is exposed to the void space and the method further comprises selecting the area to minimize or eliminate the starvation effect.

13. The method of claim 12 comprising selecting the area of openings to optimize the uptake rate for a specific chemical(s).

14. The method of claim 13 wherein the sampler container is smaller than 1.8 mL.

15. The method of claim 9 wherein sampling occurs primarily by diffusion and permeation, as compared to forced advection.

16. The method of claim 9 wherein the container has a volume of approximately 0.8 to 2.0 mL.

17. The method of claim 9 wherein the sampler container is smaller than 5.0 mL.

18. The method of claim 9 wherein the uptake rate is within the range of about 0.1 to 1 milliliter per minute (mL/min).

19. The method of claim 9 wherein the uptake rate is within the range of about 0.01 to about 10 milliliter per minute (mL/min).

20. A method of sampling to form a seal just above a passive sampler, including:
providing a plastic sleeve;
compressing a foam plug;
placing the compressed foam plug inside one end of a substantially rigid pipe;
placing a dowel inside the pipe;
placing the pipe inside the plastic sleeve;
drilling a borehole and removing soil;

providing a sampler according to claim 1;

lowering the sampler to a target depth;

lowering the plastic sleeve, pipe and dowel to a depth slightly above the passive sampler; and lifting the pipe while holding the dowel substantially stationary until the dowel extends below the bottom of the pipe, thereby forcing the foam out of the pipe and allowing it to expand, pressing the sleeve against borehole wall and forming a seal just above the passive sampler.

* * * * *